US011446384B2

(12) United States Patent
Kim et al.

(10) Patent No.: US 11,446,384 B2
(45) Date of Patent: Sep. 20, 2022

(54) AGENT FOR TARGETING HEART COMPRISING TANNIC ACID

(71) Applicants: Korea Research Institute of Chemical Technology, Daejeon (KR); Korea Advanced Institute of Science and Technology, Daejeon (KR)

(72) Inventors: Ki-Suk Kim, Daejeon (KR); Hyang-Ae Lee, Daejeon (KR); Sun Hyun Park, Daejeon (KR); Haeshin Lee, Daejeon (KR); Mikyung Shin, Daejeon (KR)

(73) Assignees: Korea Research Institute of Chemical Technology; Korea Advanced Institute of Science and Technology

( * ) Notice: Subject to any disclaimer, the term of this patent is extended or adjusted under 35 U.S.C. 154(b) by 424 days.

(21) Appl. No.: 16/482,444

(22) PCT Filed: Mar. 12, 2019

(86) PCT No.: PCT/KR2019/002833
§ 371 (c)(1),
(2) Date: Jul. 31, 2019

(87) PCT Pub. No.: WO2019/182279
PCT Pub. Date: Sep. 26, 2019

(65) Prior Publication Data
US 2020/0108149 A1   Apr. 9, 2020

(30) Foreign Application Priority Data

Mar. 22, 2018   (KR) .................. 10-2018-0033156

(51) Int. Cl.
*A61P 9/10* (2006.01)
*A61K 47/54* (2017.01)
*A61K 38/18* (2006.01)

(52) U.S. Cl.
CPC ........ *A61K 47/545* (2017.08); *A61K 38/1825* (2013.01); *A61P 9/10* (2018.01)

(58) Field of Classification Search
CPC ...... A61K 47/545; A61K 38/1825; A61P 9/10
See application file for complete search history.

(56) References Cited

U.S. PATENT DOCUMENTS

| | | |
|---|---|---|
| 2003/0009145 A1 | 1/2003 | Struijker-Boudier et al. |
| 2003/0148968 A1 | 8/2003 | Hammond et al. |
| 2005/0202050 A1 | 9/2005 | Kiel et al. |

FOREIGN PATENT DOCUMENTS

| | | |
|---|---|---|
| CN | 106344596 A | 1/2017 |
| KR | 1020000019718 A | 4/2000 |
| WO | 2006121532 A2 | 11/2006 |

OTHER PUBLICATIONS

Xiong et al. 2016; Facile immobilization of vascular endothelial growth factor on a tannic acid-functionalized plasma-polymerized allylamine coating rich in quinone groups. RSC Advances. 6: 17188-17195.*
Bry et al. 2014; Vascular endothelial growth factor-B in physiology and disease. Physiological Review. 94: 779-794.*
Anonymous, "2P-288: TANNylation: A reversible protein modification utilizing heart as a new therapeutic reservoir thesis detail paper search," Jan. 1, 2016, Retrieved online from <http://www.papersearch.net/thesis/article.asp?key=3502888> on Mar. 10, 2021, 2 pgs.
Extended European Search Report for European Patent Application No. 19770857.1, dated Mar. 22, 2021, 7 pgs.
Scott, R.C. et al., "Aiming for the heart: targeted delivery of drugs to diseased cardiac tissue," Expert Opin. Drug Deliv. 5. 459-478 (2008).
Wang, Z. et al., "Adeno-associated virus serotype 8 efficiently delivers genes to muscle and heart," Nat. Biotechnol. 23, 321-328 (2005).
Mayer, C.R. et al., "Ultrasonic gene and drug delivery to the cardiovascular system," Adv. Drug Deliver. Rev. 60. 1177-1192 (2008).
Dvir, T. et al., "Nanoparticles Targeting the Infarcted Heart," Nano Lett. 11, 4411-4414 (2011).
Beeri, R. et al., "New Efficient Catheter-Based System for Myocardial Gene Delivery," Circulation 106. 1756-1759 (2002).
Huang, H. et al., "pH-Responsive nanodrug encapsulated by tannic acid complex for controlled drug delivery," RSC Adv. 2017, 7. 2829-2835.
Xu, Y. et al., "Tannic acid as plant-derived polyphenol exerts vasoprotection via enhancing KLF2 expression in endothelial cells," Scientific reports, 2017, 7. 6686.
Hu. X. et al., "Cardioprotective Effects of Tannic Asic on Isoproterenol-Induced Myocardial Injury in Rats: Further Insight into 'French Paradox'," Phytother. Res. 29:1295-1303 (2015).

* cited by examiner

Primary Examiner — Karen Cochrane Carlson
(74) Attorney, Agent, or Firm — Fredrikson & Byron, P.A.

(57) ABSTRACT

The present invention relates to a heart targeting agent comprising tannic acid, in which the agent aids a heart disease therapeutic drug to be delivered to the heart and bind to the cardiac myocardium by inducing tannylation of the drug so as to make heart targeting and accumulation of the drug possible. Unlike the conventional invasive method used for the traditional drugs to be able to target the heart, the agent of the present invention can help a drug to target the heart with high efficiency just via non-invasive intravenous administration.

7 Claims, 26 Drawing Sheets
(12 of 26 Drawing Sheet(s) Filed in Color)
Specification includes a Sequence Listing.

[Figure 1]
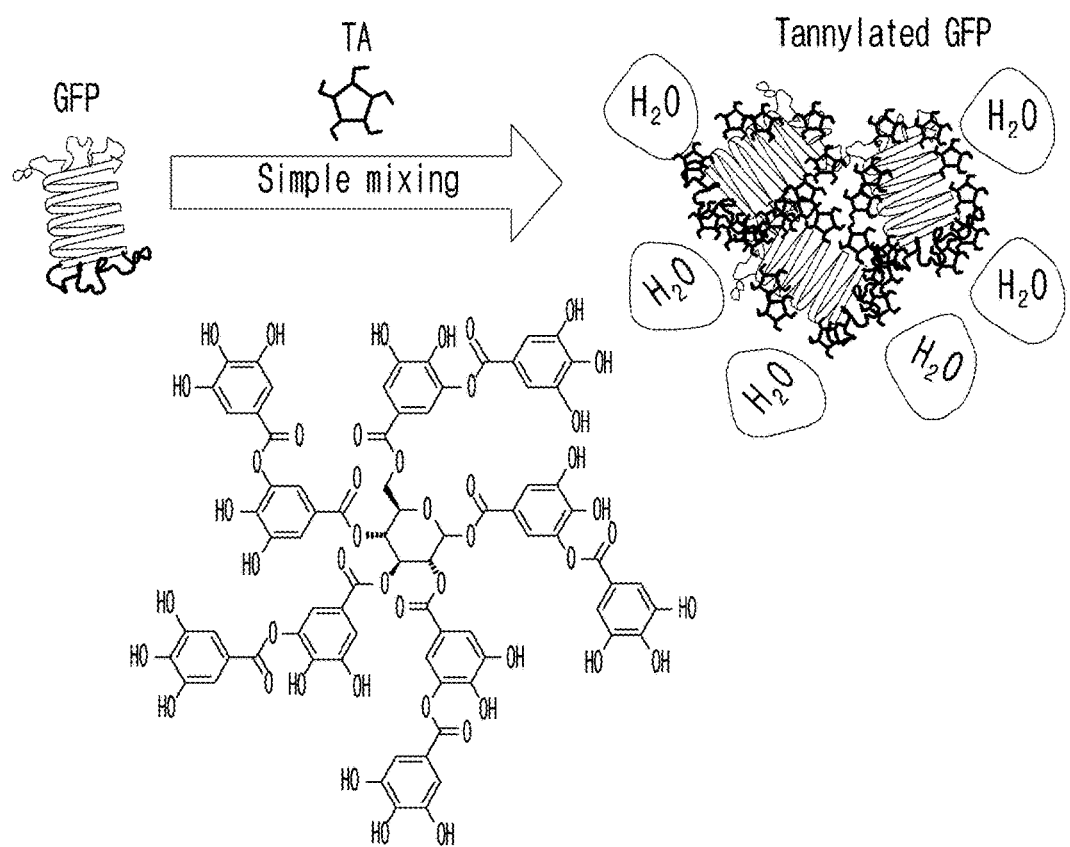

[Figure 2]
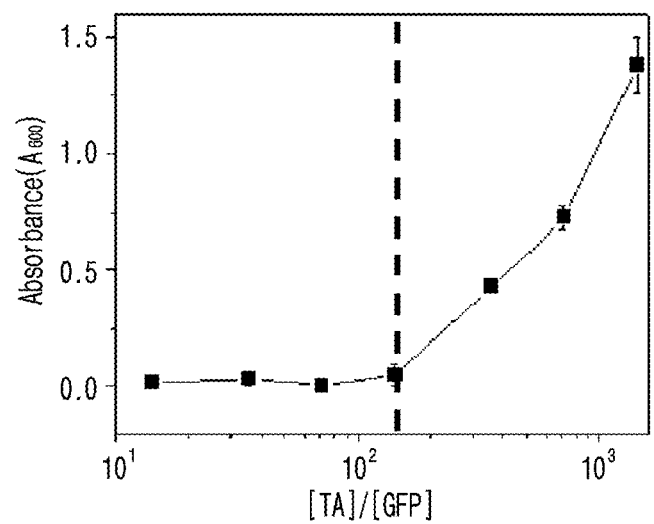

[Figure 3a]
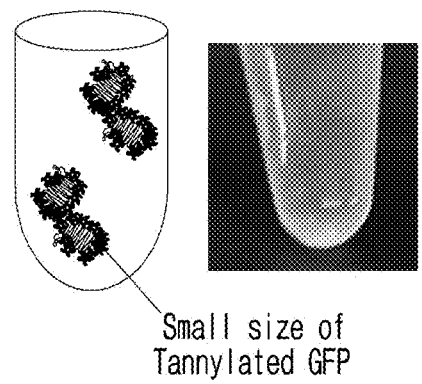
$$\frac{[TA]}{[GFP]} = 72$$
Small size of Tannylated GFP
[Figure 3b]
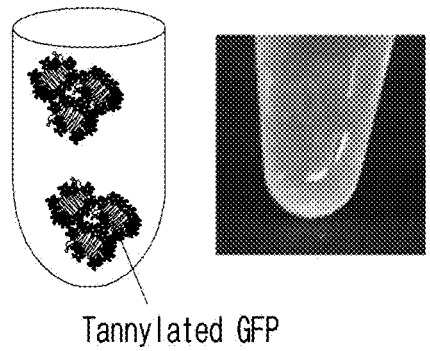
$$\frac{[TA]}{[GFP]} = 143$$
Tannylated GFP

[Figure 3c]
$$\frac{[TA]}{[GFP]} = 357$$
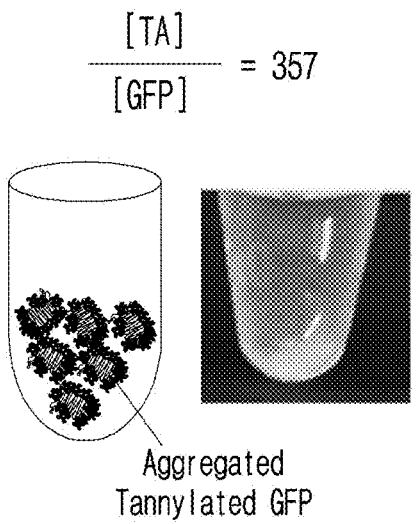
Aggregated Tannylated GFP
[Figure 4a]
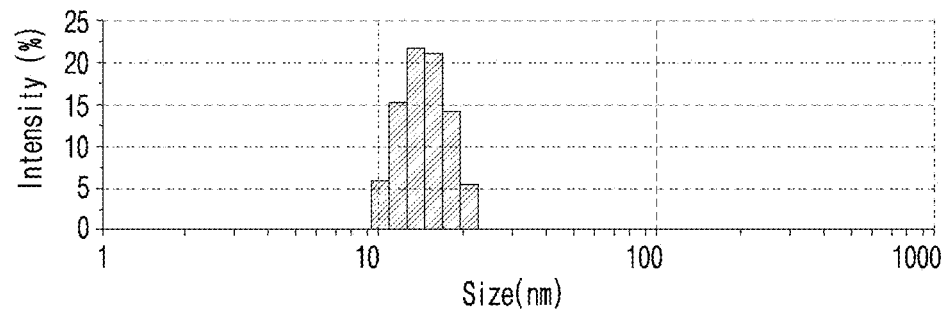
[Figure 4b]
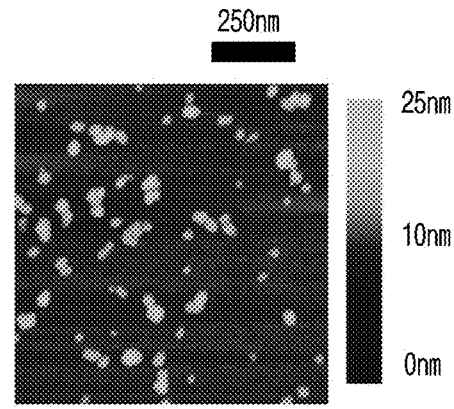

[Figure 4c]
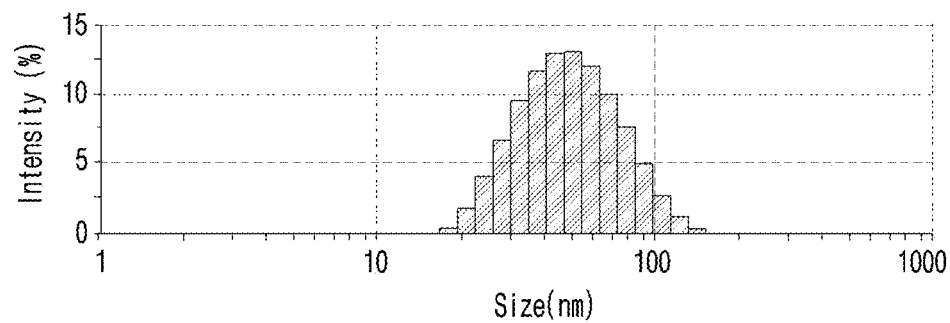
[Figure 4d]
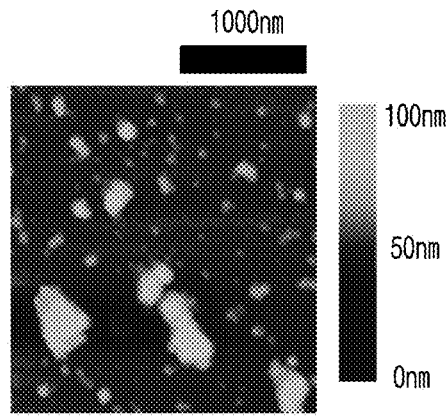
[Figure 5a]
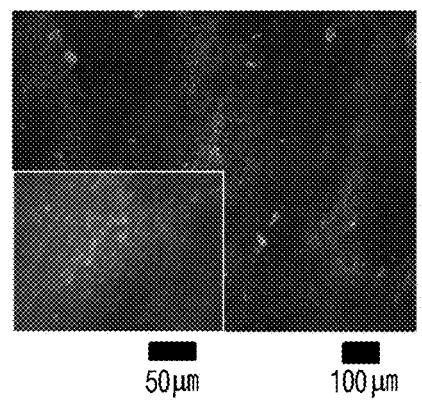

[Figure 5b]
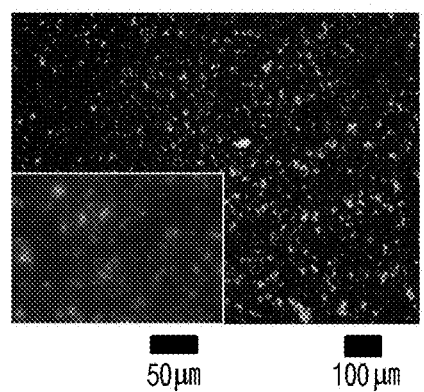
[Figure 5c]
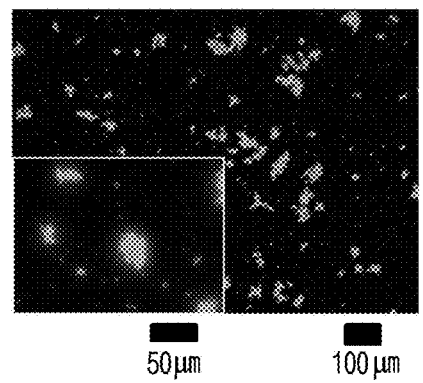
[Figure 6]
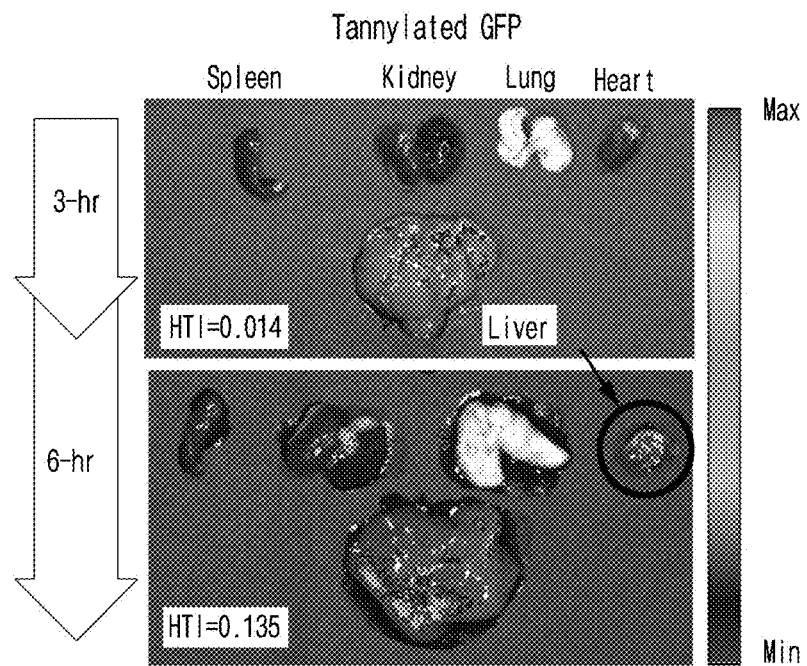

[Figure 7]
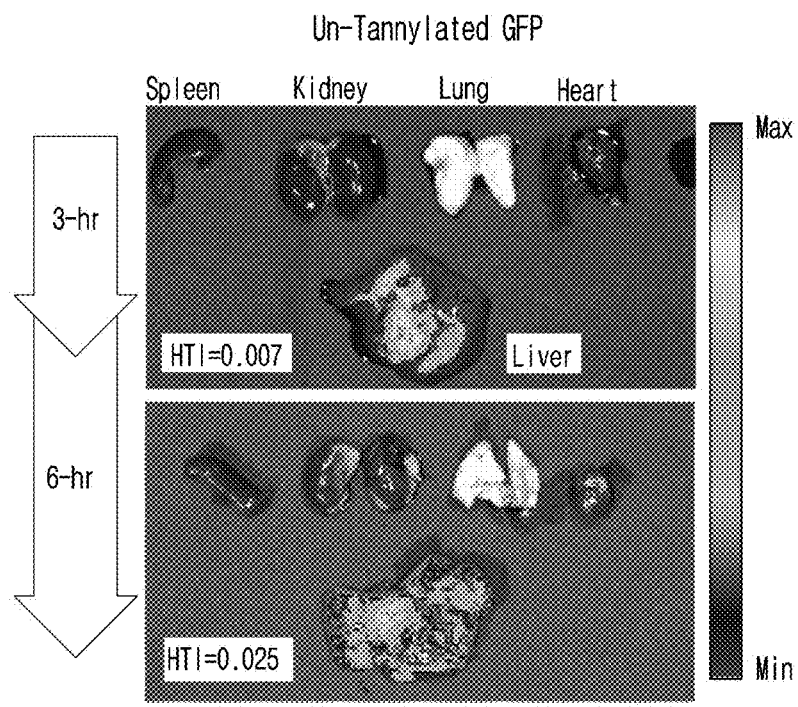
[Figure 8]
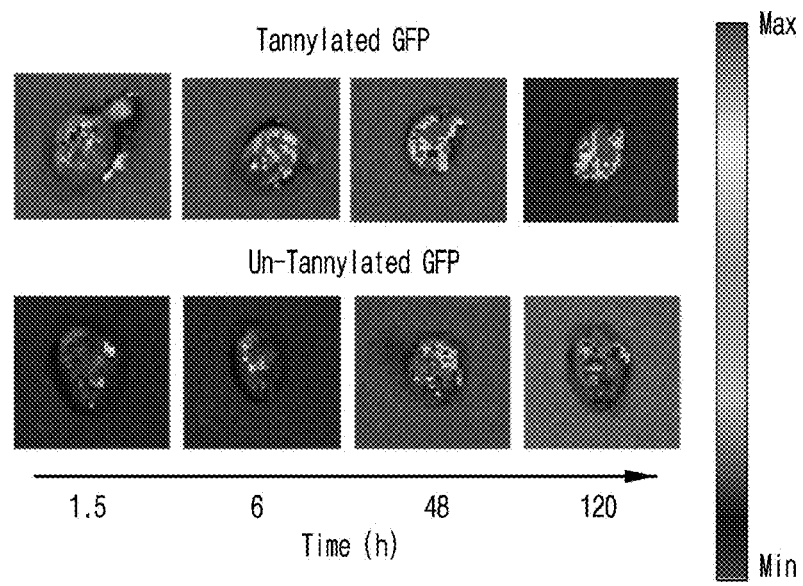

[Figure 9]
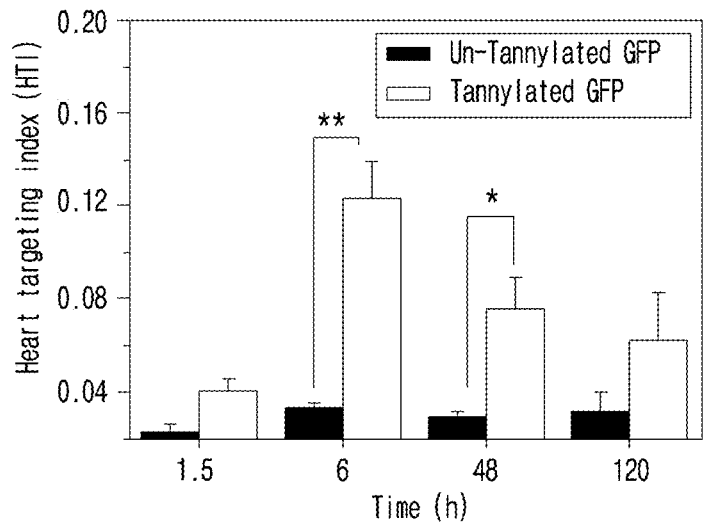
[Figure 10a]
Un-Tannylated GFP
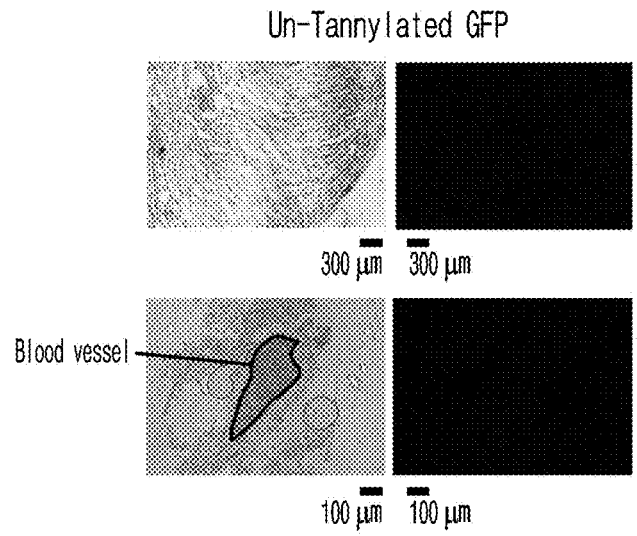

[Figure 10b]
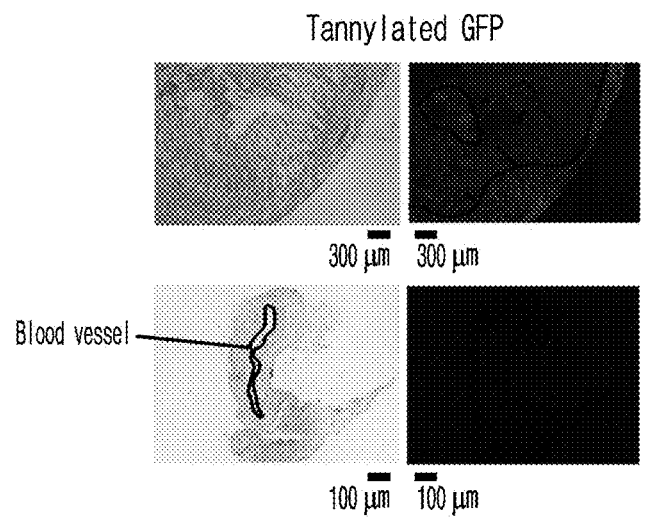
[Figure 10c]
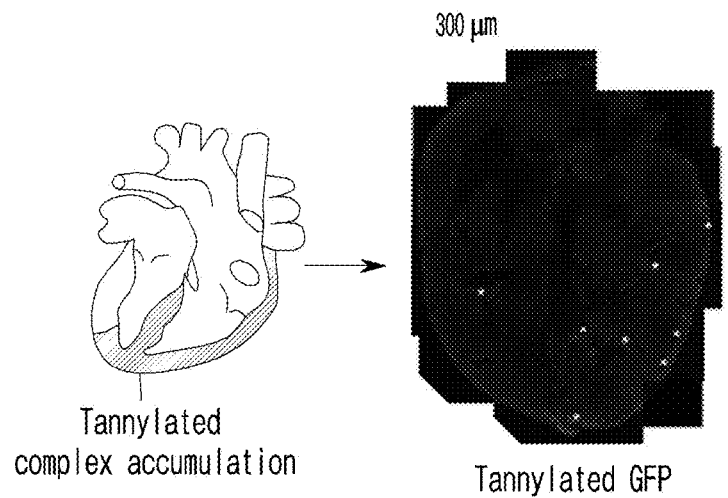

[Figure 11]
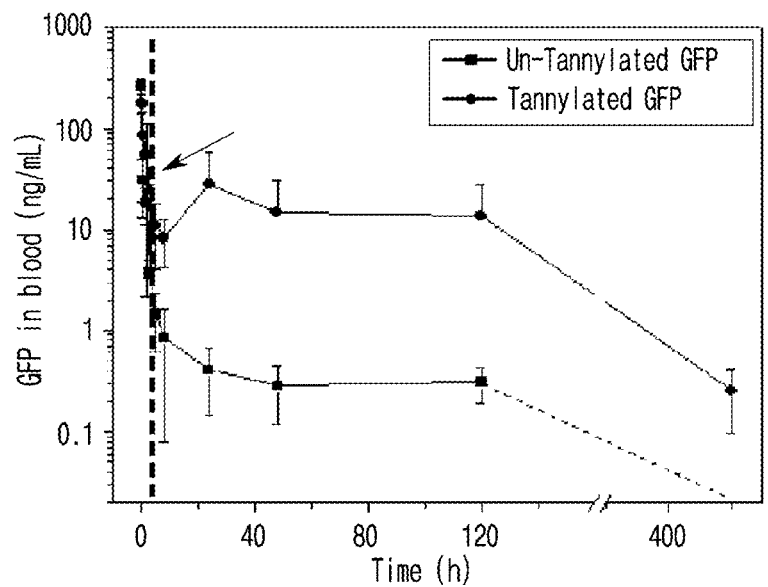
[Figure 12]
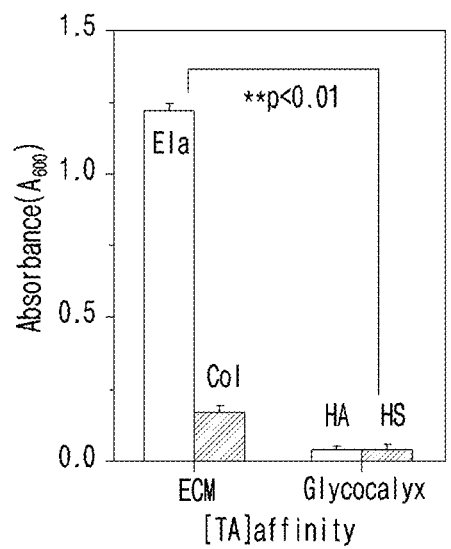

[Figure 13]
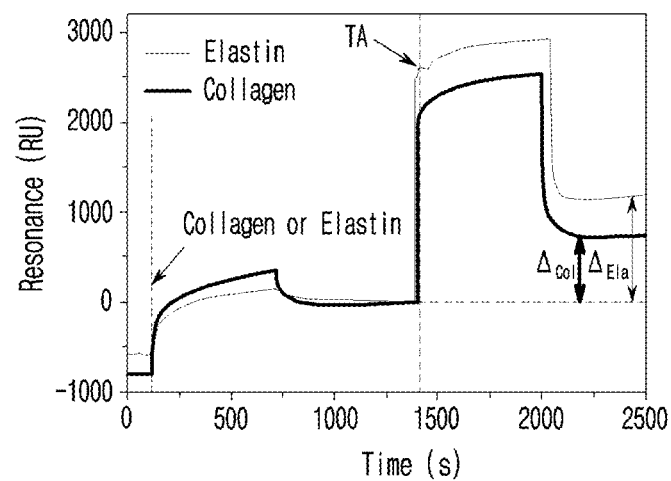
[Figure 14a]
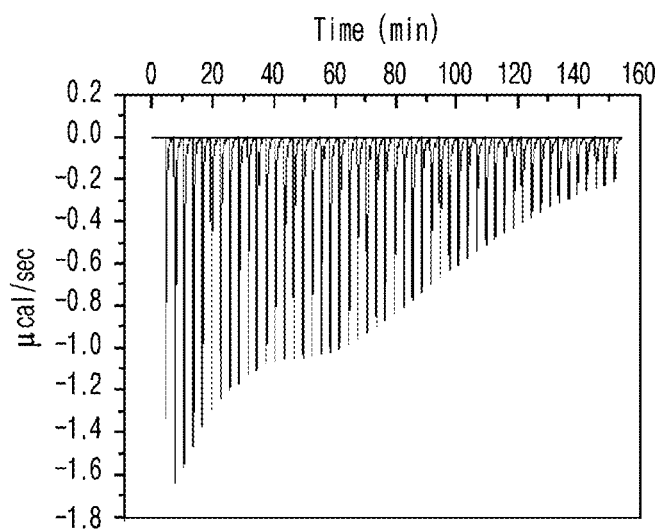

[Figure 14b]
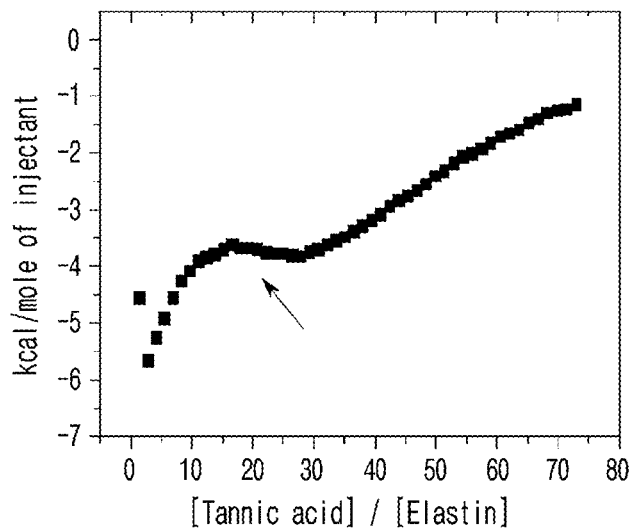
[Figure 15]
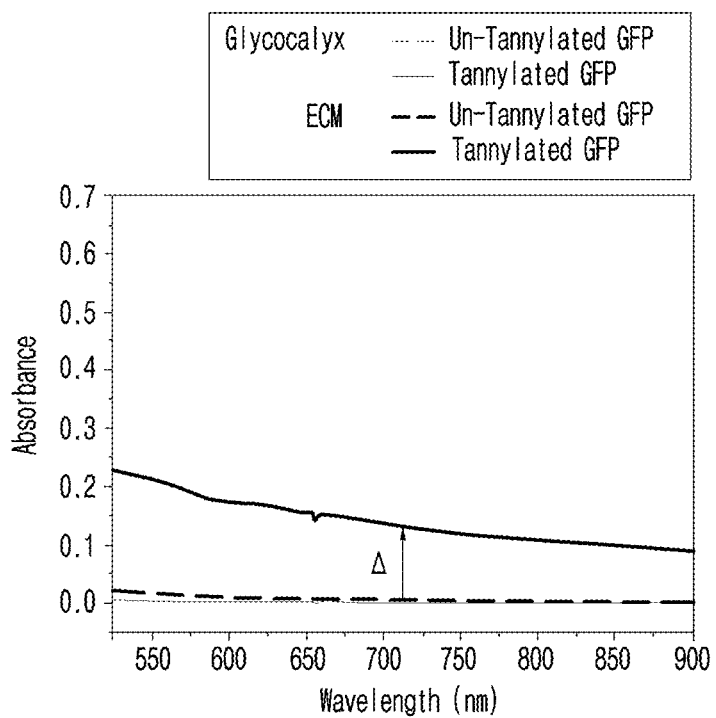

[Figure 16]
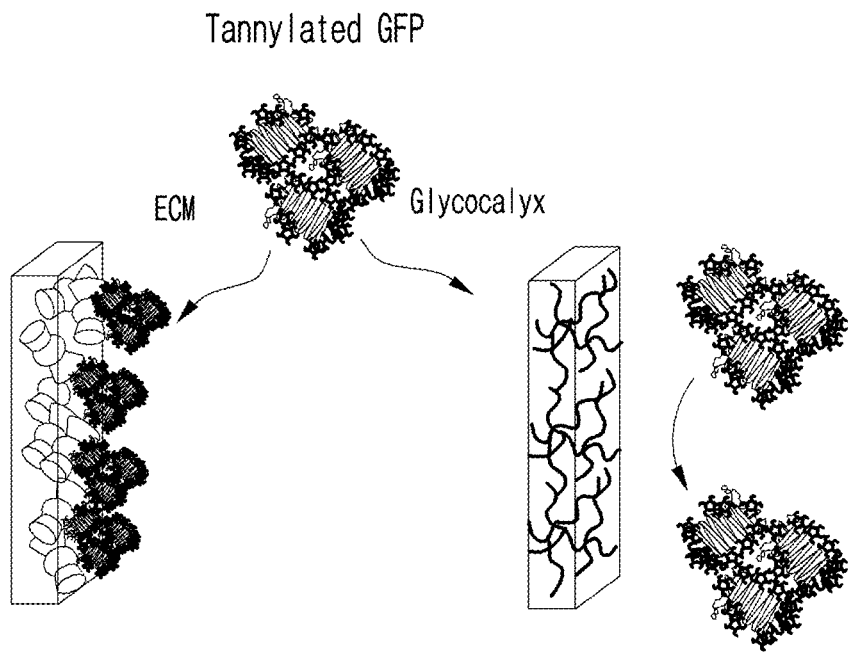
[Figure 17a]
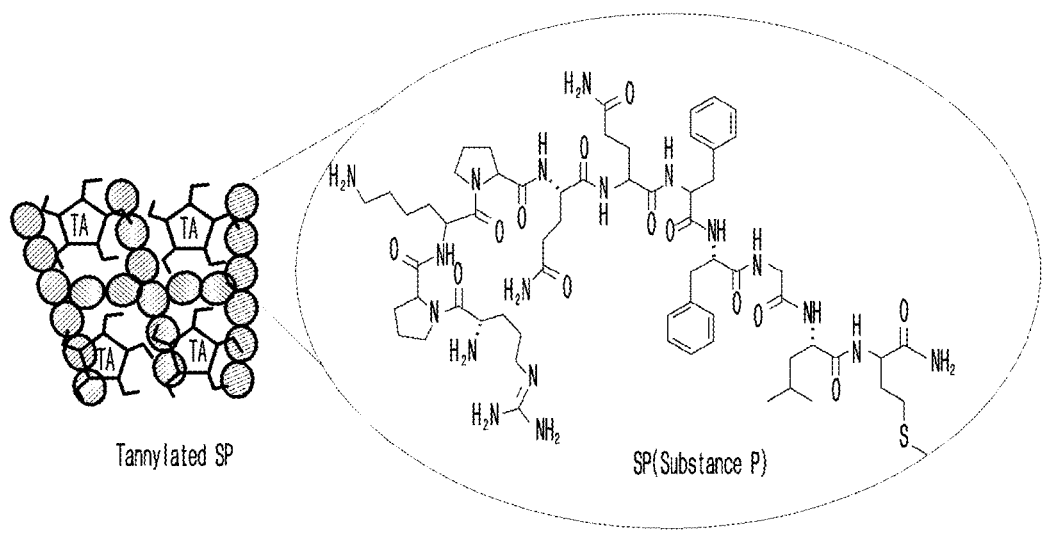

[Figure 17b]
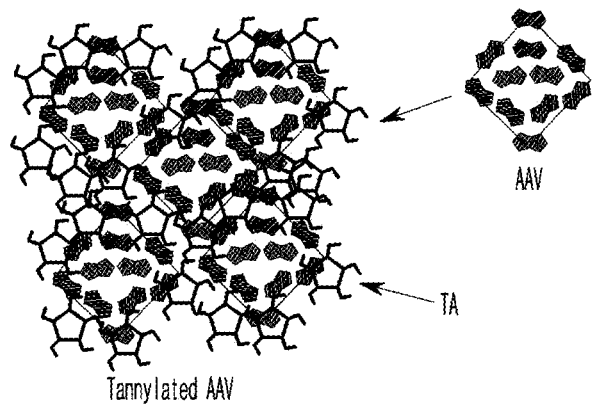
[Figure 18a]
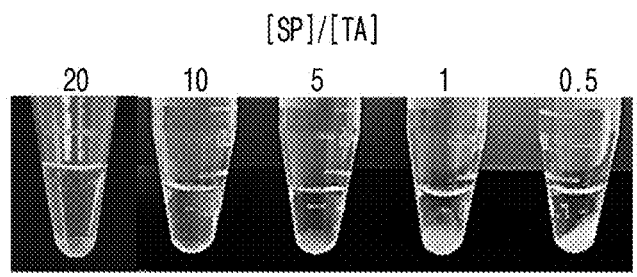
[Figure 18b]
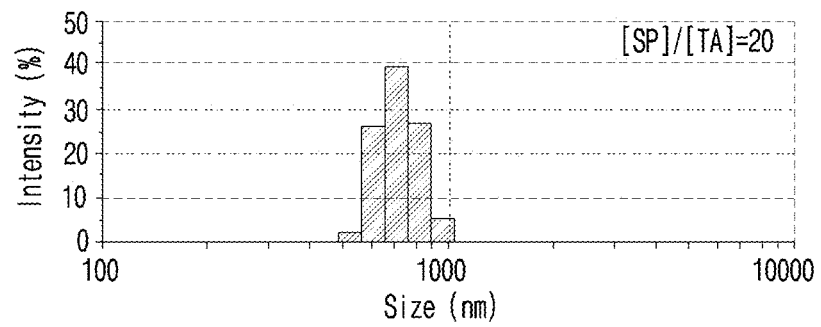
[Figure 18c]
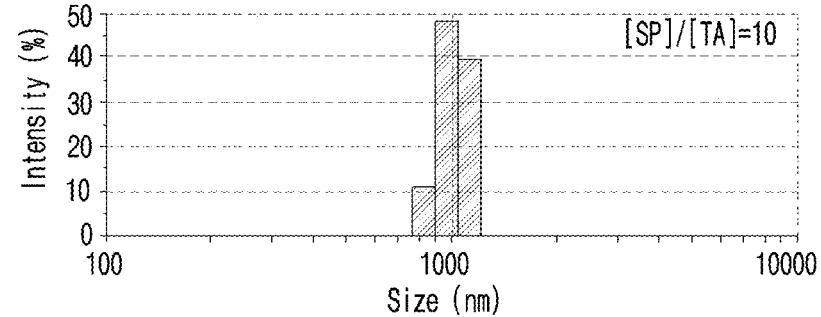

[Figure 19a]
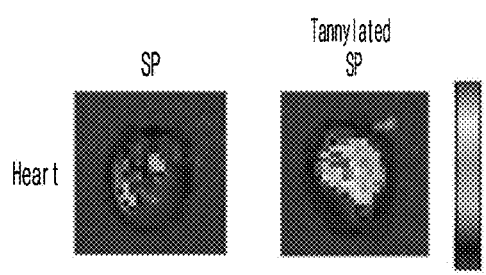
[Figure 19b]
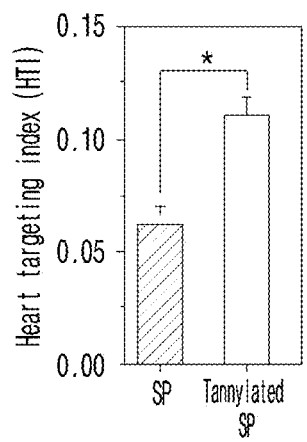

[Figure 20]
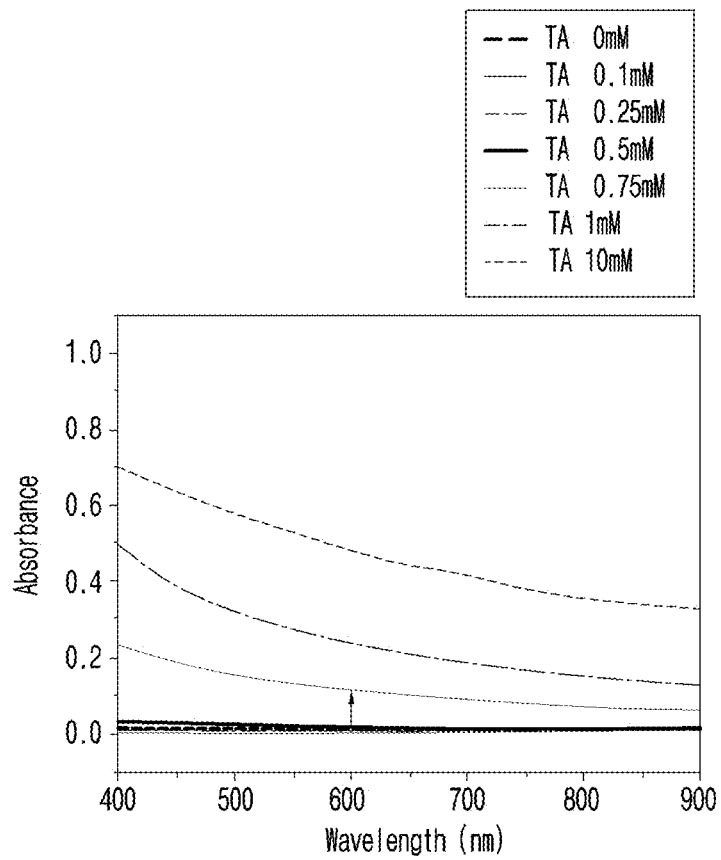
[Figure 21a]
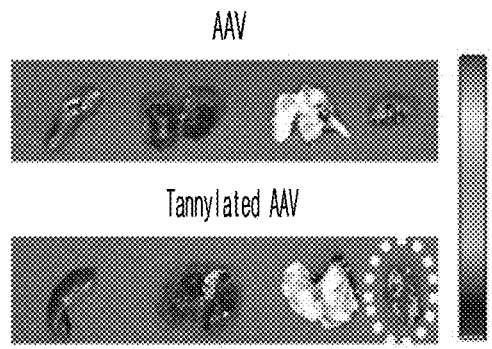

[Figure 21b]
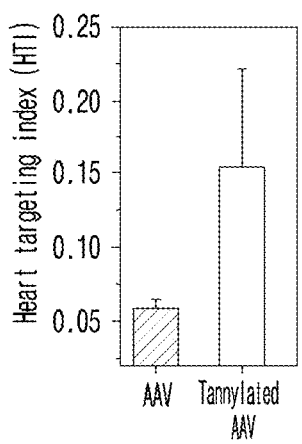
[Figure 22a]
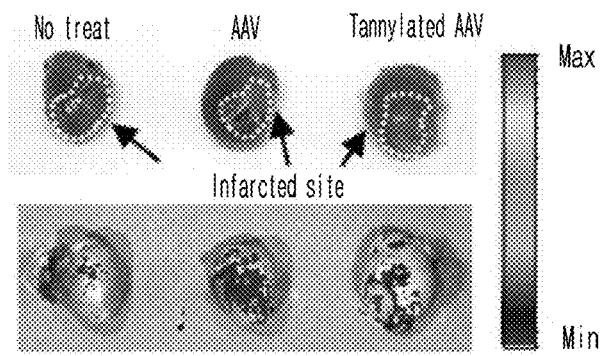
[Figure 22b]
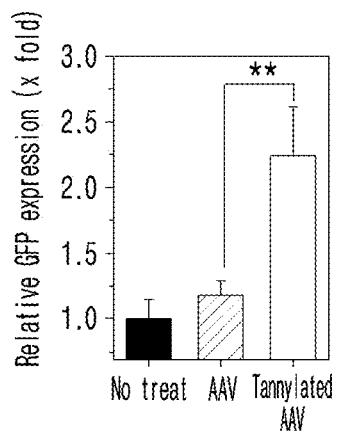

[Figure 23]
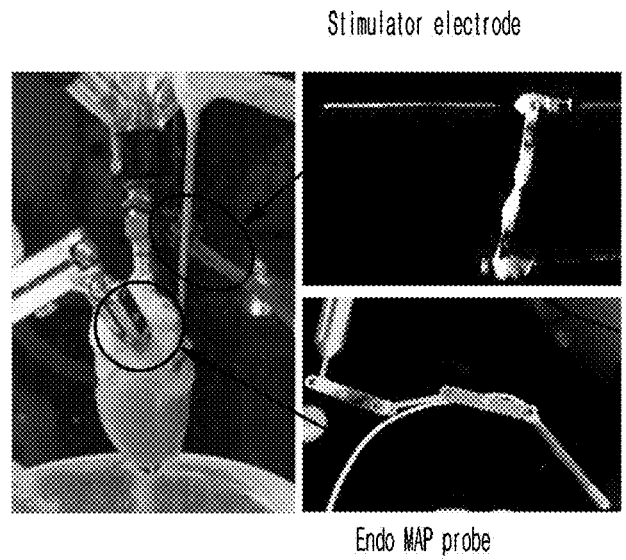
[Figure 24a]
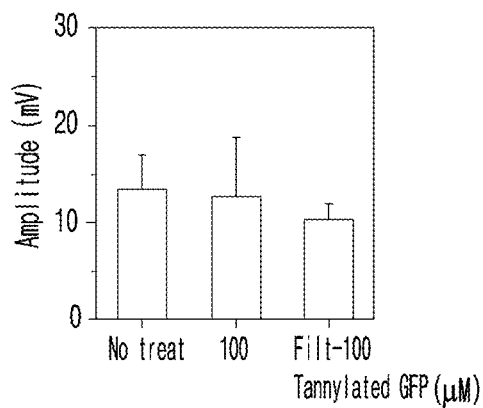
[Figure 24b]
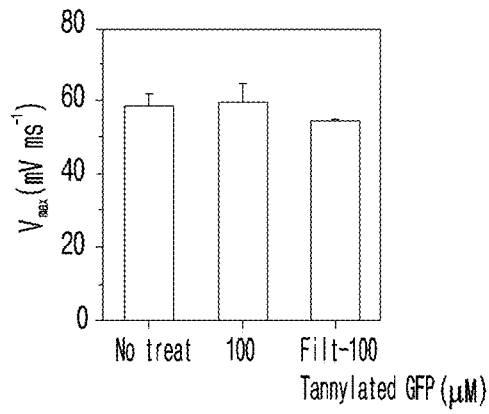

[Figure 24c]
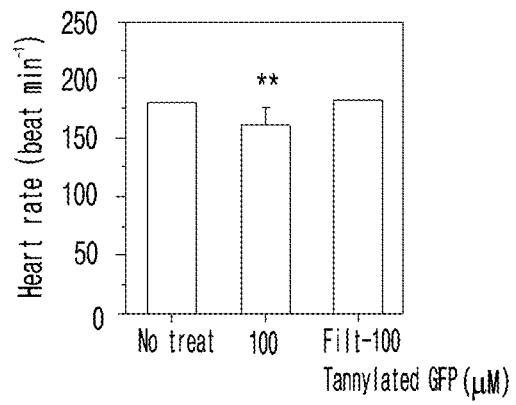
[Figure 25a]
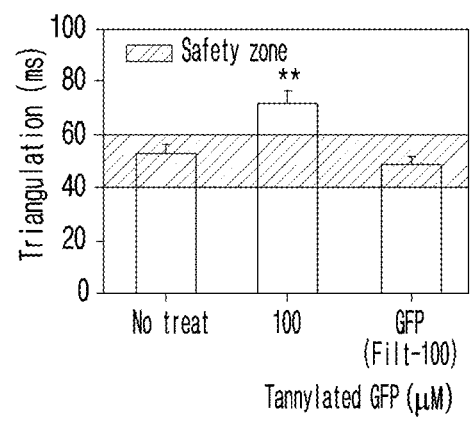
[Figure 25b]
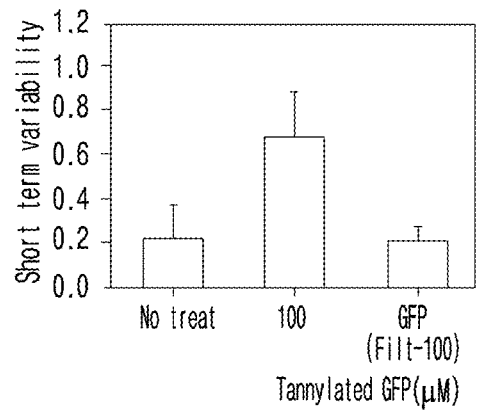

[Figure 26]
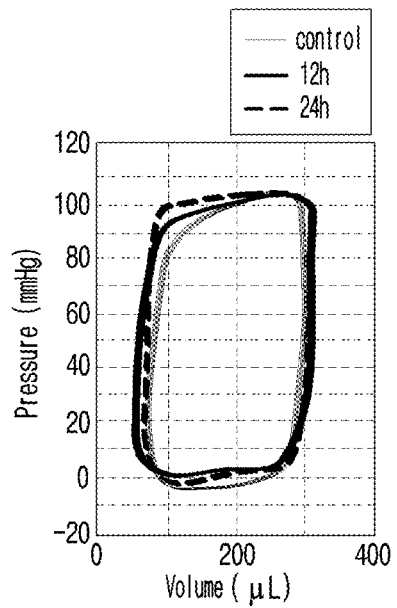
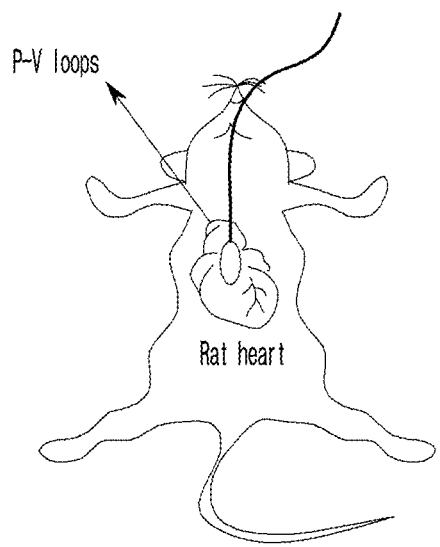

[Figure 27a]
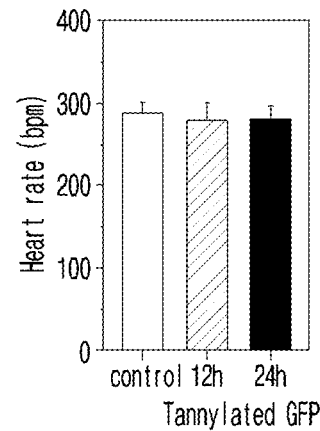
[Figure 27b]
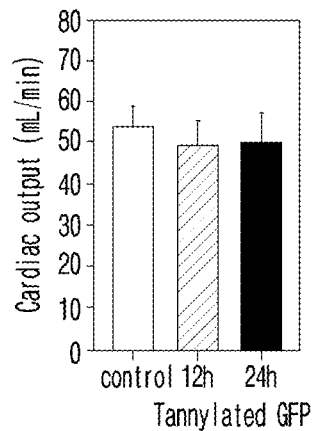
[Figure 27c]
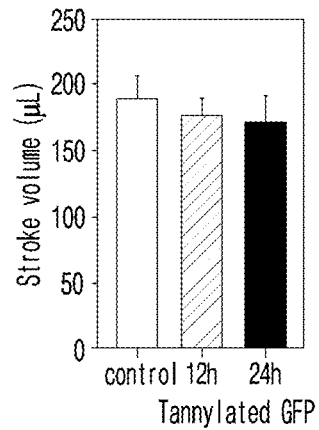

[Figure 27d]
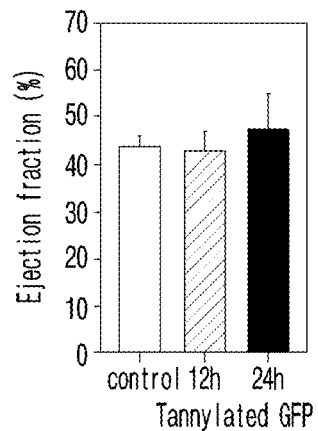
[Figure 27e]
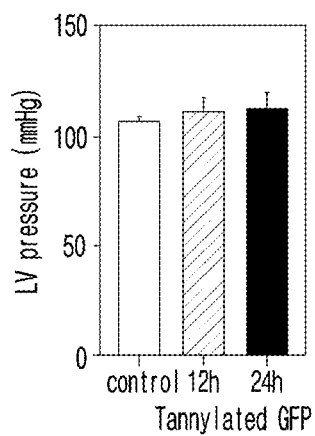
[Figure 27f]
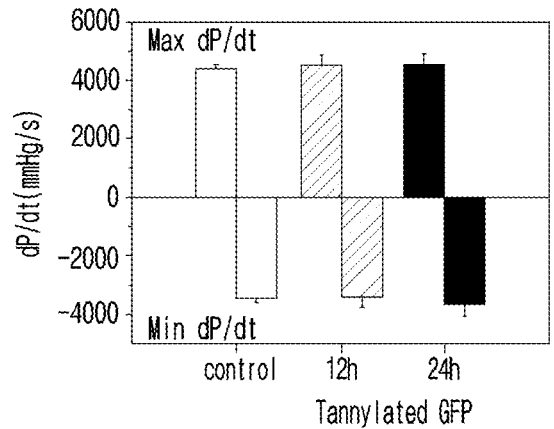

[Figure 27g]
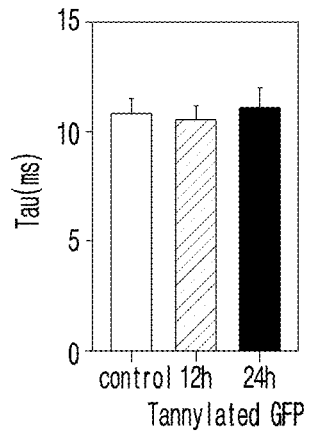
[Figure 28a]
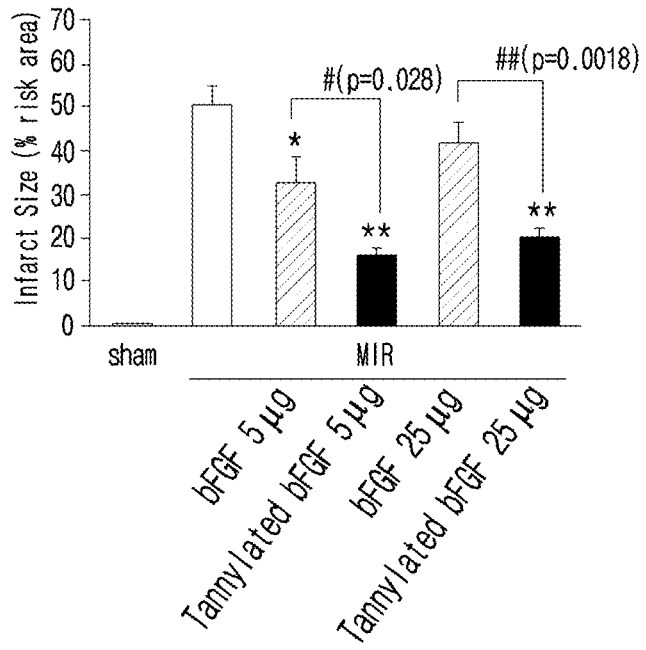

[Figure 28b]
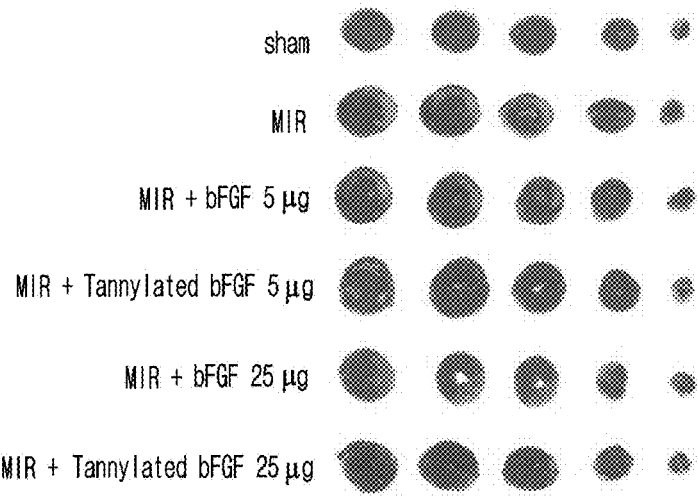
[Figure 29a]
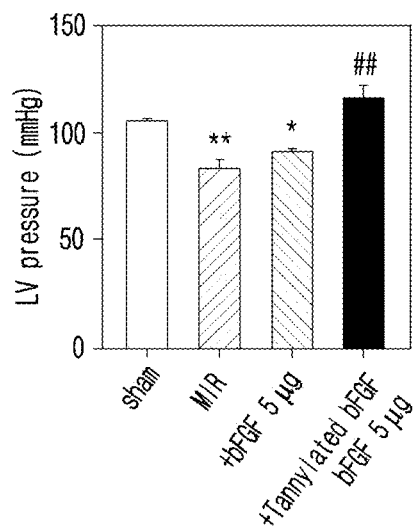
\* p<0.05, \*\* p<0.01, vs. sham
## p<0.01, vs. MIR

[Figure 29b]
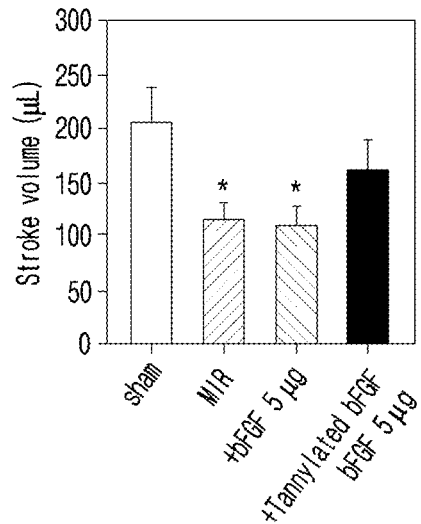
\* p<0.05, \*\* p<0.01, vs. sham
\#\# p<0.01, vs. MIR
[Figure 29c]
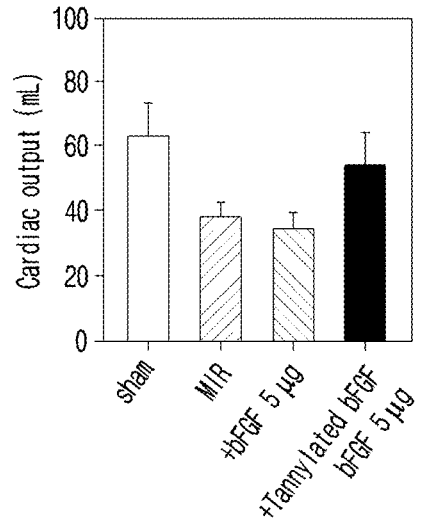
\* p<0.05, \*\* p<0.01, vs. sham
\#\# p<0.01, vs. MIR

[Figure 29d]
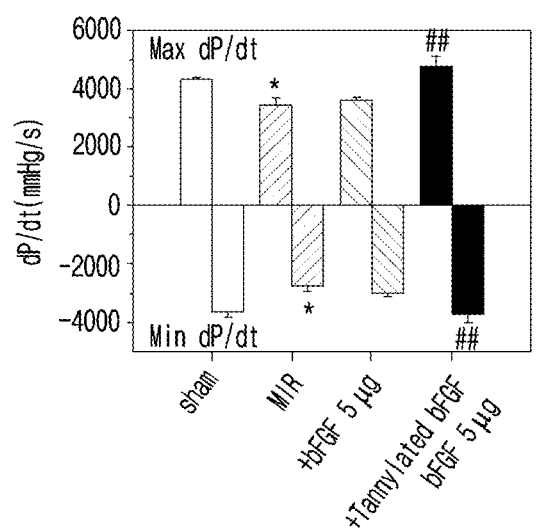
* p<0.05, ** p<0.01, vs. sham
## p<0.01, vs. MIR

```
                              SEQUENCE LISTING

<160> NUMBER OF SEQ ID NOS: 2

<210> SEQ ID NO 1
<211> LENGTH: 154
<212> TYPE: PRT
<213> ORGANISM: Artificial Sequence
<220> FEATURE:
<223> OTHER INFORMATION: bFGF(basic fibroblast growth factor)

<400> SEQUENCE: 1

Ala Ala Gly Ser Ile Thr Thr Leu Pro Ala Leu Pro Glu Asp Gly Gly
1               5                   10                  15

Ser Gly Ala Phe Pro Pro Gly His Phe Lys Asp Pro Lys Arg Leu Tyr
            20                  25                  30

Cys Lys Asn Gly Gly Phe Phe Leu Arg Ile His Pro Asp Gly Arg Val
        35                  40                  45

Asp Gly Val Arg Glu Lys Ser Asp Pro His Ile Lys Leu Gln Leu Gln
    50                  55                  60

Ala Glu Glu Arg Gly Val Val Ser Ile Lys Gly Val Cys Ala Asn Arg
65                  70                  75                  80

Tyr Leu Ala Met Lys Glu Asp Gly Arg Leu Leu Ala Ser Lys Cys Val
                85                  90                  95

Thr Asp Glu Cys Phe Phe Phe Glu Arg Leu Glu Ser Asn Asn Tyr Asn
            100                 105                 110

Thr Tyr Arg Ser Arg Lys Tyr Thr Ser Trp Tyr Val Ala Leu Lys Arg
        115                 120                 125

Thr Gly Gln Tyr Lys Leu Gly Ser Lys Thr Gly Pro Gly Gln Lys Ala
    130                 135                 140

Ile Leu Phe Leu Pro Met Ser Ala Lys Ser
145                 150

<210> SEQ ID NO 2
<211> LENGTH: 11
<212> TYPE: PRT
<213> ORGANISM: Artificial Sequence
<220> FEATURE:
<223> OTHER INFORMATION: SP(substance P)

<400> SEQUENCE: 2

Arg Pro Lys Pro Gln Gln Phe Phe Gly Leu Met
1               5                   10
```

AGENT FOR TARGETING HEART COMPRISING TANNIC ACID

Related Applications

This application is a 35 U.S.C. 371 national stage filing from International Application No. PCT/KR2019/002833, filed Mar. 12, 2019, which claims priority to Korean Application No. 10-2018-0033156, filed Mar. 22, 2018, the teachings of which are incorporated herein by reference.

BACKGROUND OF THE INVENTION

1. Field of the Invention

The present invention relates to a heart targeting agent which comprises tannic acid as an active ingredient.

2. Description of the Related Art

The most convenient way to deliver a targeted drug known so far is systemic injection. A drug administered via systemic injection can be targeted to various tumor, liver and lung tissues through passive diffusion, enhanced permeability and retention (EPR) and interaction with target organ receptors. However, direct targeting of a drug to the heart by systemic injection is a very difficult because of the constant dynamic contraction-relaxation cycle of the heart with severe volume changes. In addition, blood exchange is fast and broad, so that it is not easy for the administered drug to have a long-term effect in the heart.

In general, most methods to deliver a drug locally to the heart require surgical operations such as sternotomy or thoracotomy, which inevitably involve the incision of the patient's chest wall and bone. The most representative example is 'cell-sheet', which is applied directly to the surface of the damaged myocardium. Even though intramyocardial or epicardial injection can be considered as a non-surgical approach for the treatment, open surgery is necessary in order to accurately target the drug because of the dynamic movement of the heart. In addition to direct cardiac tissue injection, several studies using intravenous injection routes, such as cardiac gene therapy with adeno-associated viral vectors, microvesicular destruction using ultrasound, catheter-based gene delivery, and myocardial infarction-specific targeting peptides coupled with liposomes have been reported (Scott, R. C. et al., Expert Opin. Drug Deliv.5, 459-470 (2008); Wang, Z. et al., Nat. Biotechnol.23, 321-328 (2005); Mayer, C. R. & Bekeredjian, R., Adv. Drug Deliver. Rev. 60, 1177-1192 (2008); Dvir, T. et al., Nano Lett. 11, 4411-4414 (2011); Beeri, R. et al., Circulation 106, 1756-1759 (2002)). Such systemic delivery methods require delicate and challenging chemical/biological experiment settings and have disadvantages of being administered intravenously at a high concentration.

To deliver protein/peptide drugs efficiently to the heart via intravenous injection, the drug delivery vehicle must be able to recognize the organ (tissue)-specific characteristics. That is, the vehicle injected by intravenous injection should not be adsorbed to the glycocalyx layers of the vascular endothelial layer but instead to be adsorbed right away to the cardiac tissue such as the thick and ECM rich myocardium (mostly composed of elastin and collagen).

Tannic acid (TA) is one of polyphenols rich in plants such as fruits, vegetables, olive and cacao. Recently, tannic acid has been used as a multifunctional coating molecule. It is also known as a molecule having an excellent affinity with biomacromolecules including DNA and such proline-rich proteins as thrombin, gelatin, collagen and mucin. Tannic acid binds to a protein through multiple hydrogen bonds and hydrophobic interactions between the hydroxy group rich moiety (five gallol groups (three-OH groups linked to an aromatic ring) and five catechol groups (two-OH groups linked to an aromatic ring by covalent bond)) and a target protein.

SUMMARY OF THE INVENTION

It is an object of the present invention to provide a heart targeting agent comprising tannic acid as an active ingredient.

It is another object of the present invention to provide a use of a tannylated heart disease therapeutic drug for the prevention or treatment of heart disease.

It is also an object of the present invention to provide a heart targeting composition comprising a tannylated drug carrier as an active ingredient.

It is further an object of the present invention to provide a method for targeting a heart disease therapeutic drug to the heart with high efficiency comprising a step of tannylating the heart disease therapeutic drug.

It is also an object of the present invention to provide a kit for treating heart disease which comprises tannic acid and a heart disease therapeutic drug.

To achieve the above objects, the present invention provides a heart targeting agent comprising tannic acid represented by formula 1 below as an active ingredient:

[Formula 1]

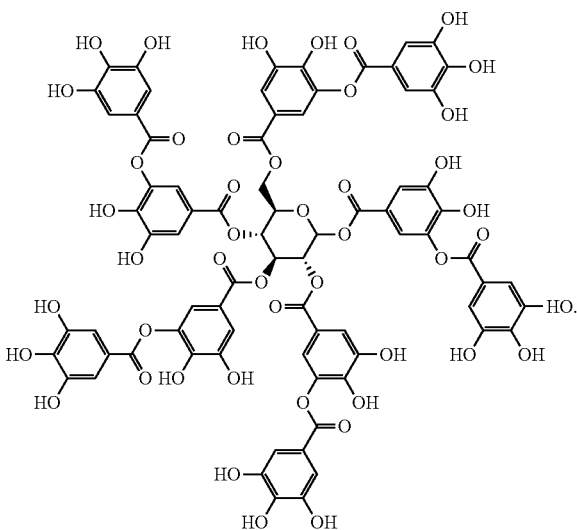

The present invention also provides a pharmaceutical composition comprising a tannylated heart disease therapeutic drug as an active ingredient for the prevention or treatment of heart disease.

The present invention also provides a heart targeting composition comprising a tannylated drug carrier as an active ingredient.

The present invention also provides a method for targeting a heart disease therapeutic drug to the heart with high efficiency comprising a step of tannylating the heart disease therapeutic drug.

The present invention also provides a kit for treating heart disease which comprises tannic acid and a heart disease therapeutic drug.

The present invention also provides a method for preventing, ameliorating or treating heart disease comprising a step of administering a tannylated heart disease therapeutic drug to a subject.

In addition, the present invention provides a use of a tannylated heart disease therapeutic drug for the production of a drug for preventing, ameliorating or treating heart disease.

Advantageous Effect

According to the present invention, a heart disease therapeutic drug to be delivered to the heart can bind to the cardiac myocardium by inducing tannylation of the drug so as to make heart targeting and accumulation of the drug possible. Unlike the conventional invasive method used for the traditional drugs to be able to target the heart, the agent of the present invention can help a drug to target the heart with high efficiency just via non-invasive intravenous administration.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a schematic diagram illustrating the preparation process of tannylated GFP.

FIG. 2 is a graph illustrating the results of a turbidity test performed to determine the critical stoichiometric ratio of [TA]/[GFP] (TA: tannic acid).

FIG. 3a presents the results of a visual observation of the appearance of tannylated GFP according to the stoichiometric ratio of [TA]/[GFP]=72.

FIG. 3b presents the results of a visual observation of the appearance of tannylated GFP according to the stoichiometric ratio of [TA]/[GFP]=143.

FIG. 3c presents the results of a visual observation of the appearance of tannylated GFP according to the stoichiometric ratio of [TA]/[GFP]=357).

FIG. 4a presents the results of a DLS analysis of size characteristics of tannylated GFP with the stoichiometric ratio of [TA]/[GFP]=72.

FIG. 4b presents the results of a AFM analysis of morphology characteristics of tannylated GFP with the stoichiometric ratio of [TA]/[GFP]=72.

FIG. 4c presents the results of a DLS analysis of size characteristics of tannylated GFP with the stoichiometric ratio of [TA]/[GFP]=143.

FIG. 4d presents the results of a AFM analysis of morphology characteristics of tannylated GFP with the stoichiometric ratio of [TA]/[GFP]=143.

FIG. 5a presents the fluorescence image of tannylated GFP with the stoichiometric ratio of 214 of [TA]/[GFP] forming a microscale complex.

FIG. 5b presents the fluorescence image of tannylated GFP with the stoichiometric ratio of 286 of [TA]/[GFP] forming a microscale complex.

FIG. 5c presents the fluorescence image of tannylated GFP with the stoichiometric ratio of 714 of [TA]/[GFP] forming a microscale complex.

FIG. 6 presents the overall distribution of tannylated GFP in organs respectively right after, 3 hours and 6 hours after the intravenous injection of the tannylated GFP to a mouse (HTI: heart-targeting index).

FIG. 7 presents the overall distribution of un-tannylated GFP in organs respectively right after, 3 hours and 6 hours after the intravenous injection of the un-tannylated GFP to a mouse (HTI: heart-targeting index).

FIG. 8 presents the accumulation of tannylated GFP and un-tannylated GFP in the mouse heart respectively right after, 1.5, 6, 48 and 120 hours after the intravenous injection of the tannylated GFP and the un-tannylated GFP to a mouse.

FIG. 9 is a graph illustrating the HTI values respectively right after, 1.5, 6, 48 and 120 hours after the intravenous injection of tannylated GFP and un-tannylated GFP to a mouse.

FIG. 10a presents the distribution pattern of un-tannylated GFP after the intravenous injection of un-tannylated GFP to a mouse (in myocardium (up) and in blood vessel (down)).

FIG. 10b presents the distribution pattern of tannylated GFP after the intravenous injection of tannylated GFP to a mouse (in myocardium (up) and in blood vessel (down)).

FIG. 10c presents the distribution pattern of tannylated GFP after the intravenous injection of tannylated GFP to a mouse (in the entire heart).

FIG. 11 is a graph illustrating the results of pharmacokinetics in blood flow after the intravenous injection of tannylated GFP and un-tannylated GFP to a mouse (blue arrow: GFP accumulation in the heart 6 hours after the injection).

FIG. 12 is a graph illustrating the turbidity of a solution caused by an inter-molecular complex formed between elastin(Ela)/collagen(Col) and tannic acid(TA); or HA(hyaluronic acid)/HS(heparin sulfate) and tannic acid(TA) (ECM: extracellular matrix).

FIG. 13 is a graph illustrating the results of SPR analysis of tannic acid bound to the surface of gold coated with collagen or elastin.

FIG. 14a presents the raw data of ITC according to the exothermic association between elastin and tannic acid.

FIG. 14b presents the data obtained by reanalyzing the raw data of FIG. 14a with a function of the molar ratio of elastin to tannic acid.

FIG. 15 is a graph illustrating the turbidity of a solution caused by the binding of the tannylated GFP to ECM; or the tannylated GFP to glycocalyx.

FIG. 16 is a schematic diagram illustrating that the tannylated protein binds to the extracellular matrix (EM) component, not to the cardiac glycocalyx.

FIG. 17(a) presents tannylated SP (Substance P) and

FIG. 17(b) presents tannylated adeno-associated virus (AAV).

FIG. 18a presents the results of a visual observation of tannylated SP according to the stoichiometric of [SP]/[TA] ([SP]/[TA]=0.5, 1, 5, 10 and 20).

FIG. 18b presents the size distribution of tannylated SP with the stoichiometric ratio of 20 of [SP]/[TA].

FIG. 18c presents the size distribution of tannylated SP with the stoichiometric ratio of 10 of [SP]/[TA].

FIG. 19(a) presents the accumulation of SP and tannylated m-Cherry-SP (tannylated SP) complex in the heart, and FIG. 19(b) presents the HTI values of SP and tannylated m-Cherry-SP (tannylated SP) complex 6 hours after the intravenous injection to a mouse.

FIG. 20 is a graph illustrating the results of the turbidity test performed to determine the maximum critical concentration of tannic acid for the preparation of tannylated AAV9 (red arrow: changes in turbidity according to the addition of tannic acid (0.75 mM)).

FIG. 21(*a*) presents the in vivo cardiac accumulation of AAV and tannylated AAV complex, and FIG. 21(*b*) is a graph illustrating the HTI values obtained 6 hours after the intravenous injection of AAV and tannylated AAV complex to a mouse.

FIG. 22(*a*) presents the GFP expression images in the infarcted heart tissue of mice not-treated or treated with AAV and tannylated AAV complex via intravenous injection, and FIG. 22(*b*) is a graph illustrating the results of quantification of GFP expression of (a).

FIG. 23 presents the experiment setup of Langendorff system connected to the heart to confirm the effect of tannylated GFP on the rat monophasic action potentials (MAP) (left), the inserted stimulating electrodes (upper right) and the MAP probe (lower right).

FIG. 24*a* present the monophasic action potentials (MAP) (Amplitude) in the heart of mice not-treated or treated with unfiltered (100) of filtered tannylated GFP (Filt-100).

FIG. 24*b* present the monophasic action potentials (MAP) (Vmax) in the heart of mice not-treated or treated with unfiltered (100) of filtered tannylated GFP (Filt-100).

FIG. 24*c* present the monophasic action potentials (MAP) (Heart rate) in the heart of mice not-treated or treated with unfiltered (100) of filtered tannylated GFP (Filt-100).

FIG. 25*a* present the monophasic action potentials (MAP) (Triguation) in the heart of mice not-treated or treated with unfiltered (100) of filtered tannylated GFP (Filt-100).

FIG. 25*b* present the monophasic action potentials (MAP) (Short term variability; STV) in the heart of mice not-treated or treated with unfiltered (100) of filtered tannylated GFP (Filt-100).

FIG. 26 illustrates the cardiac hemodynamic experiment performed with the rat heart using a pressure-volume conductance catheter technique.

FIG. 27*a* is a set of graphs illustrating the results of heart rate of the cardiac hemodynamic experiment with the mice at 12 and 24 hours after the intravenous injection of GFP (control, 6 µg/mL) or tannylated GFP (500 µl/kg).

FIG. 27*b* is a set of graphs illustrating the results of cardiac output of the cardiac hemodynamic experiment with the mice at 12 and 24 hours after the intravenous injection of GFP (control, 6 µg/mL) or tannylated GFP (500 µl/kg).

FIG. 27*c* is a set of graphs illustrating the results of stroke volume of the cardiac hemodynamic experiment with the mice at 12 and 24 hours after the intravenous injection of GFP (control, 6 µg/mL) or tannylated GFP (500 µl/kg).

FIG. 27*d* is a set of graphs illustrating the results of ejection fraction of the cardiac hemodynamic experiment with the mice at 12 and 24 hours after the intravenous injection of GFP (control, 6 µg/mL) or tannylated GFP (500 µl/kg).

FIG. 27*e* is a set of graphs illustrating the results of LV pressure of the cardiac hemodynamic experiment with the mice at 12 and 24 hours after the intravenous injection of GFP (control, 6 µg/mL) or tannylated GFP (500 µl/kg).

FIG. 27*f* is a set of graphs illustrating the ventricular contractility index of ejection fraction of the cardiac hemodynamic experiment with the mice at 12 and 24 hours after the intravenous injection of GFP (control, 6 µg/mL) or tannylated GFP (500 µl/kg).

FIG. 27*g* is a set of graphs illustrating the results of Tau value of the cardiac hemodynamic experiment with the mice at 12 and 24 hours after the intravenous injection of GFP (control, 6 µg/mL) or tannylated GFP (500 µl/kg).

FIG. 28*a* presents the result of quantifying the infarct size of the heart tissue measured 28 days after the intravenous injection of bFGF alone (5 µg or 25 µg) or tannylated bGFG (5 µg or 25 µg) to MIR (myocardial ischemia reperfusion) mouse model.

FIG. 28*b* presents the infarct site image of the heart tissue measured 28 days after the intravenous injection of bFGF alone (5 µg or 25 µg) or tannylated bGFG (5 µg or 25 µg) to MIR (myocardial ischemia reperfusion) mouse model; Sham: a group with a healthy heart.

FIG. 29*a* presents the results of LV pressure of the hemodynamic experiment performed 28 days after the intravenous injection of bFGF alone (5 µg or 25 µg) or tannylated bFGF (5 µg or 25 µg) to MIR (myocardial ischemia reperfusion) mouse model.

FIG. 29*b* presents the results of stroke volume of the hemodynamic experiment performed 28 days after the intravenous injection of bFGF alone (5 µg or 25 µg) or tannylated bFGF (5 µg or 25 µg) to MIR (myocardial ischemia reperfusion) mouse model.

FIG. 29*c* presents the results of cardiac output of the hemodynamic experiment performed 28 days after the intravenous injection of bFGF alone (5 µg or 25 µg) or tannylated bFGF (5 µg or 25 µg) to MIR (myocardial ischemia reperfusion) mouse model.

FIG. 29*d* presents the results of dP/dt of the hemodynamic experiment performed 28 days after the intravenous injection of bFGF alone (5 µg or 25 µg) or tannylated bFGF (5 µg or 25 µg) to MIR (myocardial ischemia reperfusion) mouse model; Sham: a group with a healthy heart.

DESCRIPTION OF THE PREFERRED EMBODIMENTS

Hereinafter, the present invention is described in detail.

The present invention provides a heart targeting agent comprising tannic acid represented by formula 1 below as an active ingredient:

[Formula 1]

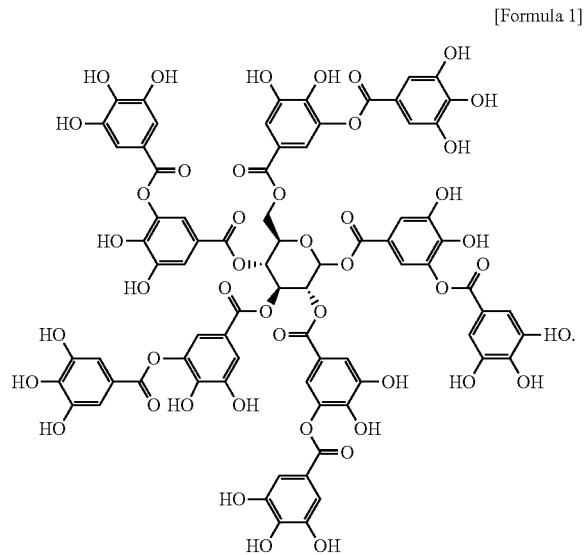 [SMILES: O=C(OC[C@H]1OC(OC(=O)c2cc(O)c(O)c(OC(=O)c3cc(O)c(O)c(O)c3)c2)[C@H](OC(=O)c2cc(O)c(O)c(OC(=O)c3cc(O)c(O)c(O)c3)c2)[C@@H](OC(=O)c2cc(O)c(O)c(OC(=O)c3cc(O)c(O)c(O)c3)c2)[C@@H]1OC(=O)c1cc(O)c(O)c(OC(=O)c2cc(O)c(O)c(O)c2)c1)c1cc(O)c(O)c(OC(=O)c2cc(O)c(O)c(O)c2)c1]

In this invention, the term "targeting" means that any substance moves massively and/or rapidly to a target such as a specific cell, a specific tissue or a specific organ in the living body. In this invention, the term "targeting agent" means a substance capable of targeting any substance to the specific target through direct or indirect binding. The targeting agent can bind directly to cells of a target tissue or a target organ or can bind to an extracellular matrix or can be absorbed in the cells, but not always limited thereto.

The targeting agent of the present invention can be composed of the said tannic acid alone, or can include other constituents such as other targeting agents, carriers, components that promote or stabilize the binding to the drug, components to protect tannic acid in use for the drug preparation or in the case of storage of the prepared drug, or spacers that spatially separate the drug, in addition to tannin. The targeting agents of the present invention can be conjugated to any carrier or drug to target the carrier or the drug to the heart.

The substance or object to be targeted by the targeting agent of the present invention is not particularly limited, but is preferably in a proper size suitable for the physical movement from the administration point to the heart or near the heart. Therefore, the targeting agent of the present invention is able to deliver an object such as a drug release system composed of at least one of a vector, a viral particle and a cell and a micro-machine as well as a substance such as an atom, a molecule, a compound, a protein, a nucleic acid and a protein/nucleic acid complex. The substance or the object above is supposed to be able to label a specific cell in the heart tissue, which is preferably a heart disease therapeutic drug, but not always limited thereto. The substance or the object above is preferably tannylated. In this invention, the term "tannylation" indicates a process in which tannic acid is attached to a substance capable of forming hydrogen bonding or hydrophobic interactions with tannic acid. Particularly, tannic acid has a phenolic hydroxy group rich moiety (gallol group and catechol group), so that it can be interacted with a substance to be tannylated through multiple hydrogen bonds and hydrophobic interaction. The tannylated substance is accumulated in the heart and then slowly released according to the gradual degradation of ester bond of tannic acid.

The said tannic acid is one of the flavonoid-based compounds represented by formula 1, which shows a non-significant adhesion to the glycocalyx layers of the cardiovascular endothelial layer, but displays a strong adhesion to the extracellular matrix (ECM) rich myocardium. Therefore, it is suggested that tannic acid can be targeted to the heart, more specifically to the myocardium of the heart and can be accumulated in the myocardium.

The present invention also provides a pharmaceutical composition comprising a tannylated heart disease therapeutic drug as an active ingredient for the prevention or treatment of heart disease.

The tannylated heart disease therapeutic drug can be targeted to the heart, more preferably to the myocardium of the heart and can be accumulated in the myocardium.

The said heart disease therapeutic drug can be any heart disease therapeutic drug known to those in the art, as long as it is a therapeutic drug can be tannylated. The said heart disease can include all the heart diseases known to those in the art. Particularly, the target heart disease can be different according to the therapeutic effect of the tannylated heart disease therapeutic drug. For example, if the heart disease therapeutic drug above is bFGF, the heart disease would be ischemic heart disease which can be selected from the group consisting of myocardial infarction, heart failure and angina pectoris.

The heart disease therapeutic drug above can be one or more substances selected from the group consisting of a compound, a protein, a nucleic acid and a protein/nucleic acid complex, which is preferably bFGF (basic fibroblast growth factor), SP (substance P), EGF (Epidermal growth factor) or VFGF-B (vascular endothelial growth factor B), but not always limited thereto.

The said bFGF can be composed of the amino acid sequence represented by SEQ ID NO: 1.

The said SP can be composed of the amino acid sequence represented by SEQ ID NO: 2.

TABLE 1

| SEQ ID NO: | Peptide | Amino acid sequence |
|---|---|---|
| 1 | bFGF | AAGSITTLP ALPEDGGSGA FPPGHFKDPK RLYCKNGGFF LRIHPDGRVD GVREKSDPHI KLQLQAEERG VVSIKGVCAN RYLAMKEDGR LLASKCVTDE CFFFERLESN NYNTYRSRKY TSWYVALKRT GQYKLGSKTG PGQKAILFLP MSAKS |
| 2 | SP | RPKPQQFFGLM |

The heart disease therapeutic drug above can use virus as a carrier. The virus can be tannylated by hydrogen bond and hydrophobic interaction between the proteins existing on the surface of the virus and tannic acid. The therapeutic agent using the virus as a carrier can be a therapeutic gene (polynucleotide sequence) that has a therapeutic or preventive effect upon expression in the heart. The said virus can be selected from the group consisting of retrovirus, adenovirus, adeno-associated virus and lentivirus. More preferably, it can be adeno-associated virus serotype 9 (AAV9).

The composition above can be administered either orally or parenterally, and the parenteral administration includes intracranial injection, intravenous injection, subcutaneous injection, intramuscular injection, intraperitoneal injection, transdermal administration and the like, and intravenous injection is more preferred.

The said bFGF can be administered at the dose of 5 to 200 μg/kg, preferably at the dose of 15 to 120 μg/kg.

The present invention also provides a heart targeting composition comprising a tannylated drug carrier as an active ingredient.

In this invention, the term "tannylation" indicates a process in which tannic acid is attached to a substance capable of forming hydrogen bonding or hydrophobic interactions with tannic acid. By the process above, a drug targeting the heart can be tannylated or a drug carrier carrying the drug targeting the heart can be tannylated.

The said drug carrier can be used without limitation as long as it has a functional group capable of forming hydrogen bonding and hydrophobic interaction with tannic acid. The drug carrier above can be preferably selected from the group consisting of a vector, a virus and a cell, but not always limited thereto.

The said virus can be selected from the group consisting of retrovirus, adenovirus, adeno-associated virus and lentivirus.

The composition above can be administered either orally or parenterally, and the parenteral administration includes intracranial injection, intravenous injection, subcutaneous injection, intramuscular injection, intraperitoneal injection, transdermal administration and the like, and intravenous injection is more preferred.

The present invention also provides a method for targeting a heart disease therapeutic drug to the heart with high efficiency comprising a step of tannylating the heart disease therapeutic drug.

The tannylation above can be accomplished by mixing a solution containing tannic acid and a solution containing a heart disease therapeutic drug. At the time of mixing, the heart disease therapeutic drug and tannic acid can be mixed at the appropriate stoichiometric ratio according to the size, shape and stability of the heart disease therapeutic drug.

The present invention also provides a kit for treating heart disease which comprises tannic acid and a heart disease therapeutic drug.

A heart disease therapeutic drug can be tannylated by mixing tannic acid and the heart disease therapeutic drug. The tannic acid and the heart disease therapeutic drug can be provided as being dissolved in a solution respectively or as being included in a kit as solutions. However, the form of the tannic acid and the heart disease therapeutic drug is not limited as long as the heart disease therapeutic drug can be tannylated by mixing the tannic acid and the heart disease therapeutic drug. The kit for treating heart disease above can additionally include s carrier, a diluent, an excipient or a combination of at least two of them commonly used in a pharmaceutical composition, and one or more heart disease therapeutic drugs can be included in the kit.

In a preferred embodiment of the present invention, the present inventors prepared tannylated GFP by mixing tannic acid (TA) and GFP with various stoichiometric ratios. Then, a tannylated GFP with a stoichiometric ratio of [TA]/[GFP] of 143, which corresponds to a reasonable range for in vivo circulation, was selected (see FIGS. 1~5).

The present inventors administered tannylated GFP to a mouse via intravenous injection, and evaluated the intestinal targeting ability thereof. As a result, it was confirmed that the tannylated GFP was specifically targeted to the heart compared to the spleen, kidney, lung, and liver (see FIGS. 6 and 7).

The present inventors administered tannylated GFP to a mouse via intravenous injection, and evaluated the heart targeting capacity thereof over the time. As a result, the tannylated GFP was found to be targeted to the heart 6 hours after the intravenous injection and maintained the heart targeting capacity for up to 120 hours, confirming that the tannylated GFP was accumulated in the heart (see FIGS. 8 and 9).

The present inventors administered tannylated GFP to a mouse via intravenous injection, and examined the spatial distribution of the tannylated GFP in the heart tissue. As a result, it was confirmed that the tannylated GFP was accumulated mostly in the myocardium (see FIG. 10).

The present inventors administered tannylated GFP to a mouse via intravenous injection, and measured the blood circulation time of the tannylated GFP. As a result, it was confirmed that the blood circulation time of the tannylated GFP was relatively longer than that of the non-tannylated GFP and remained in the blood up to 120 hours after the intravenous injection (see FIG. 11).

The present inventors also compared the ability of TA to bind to heparin sulfate (HS) and hyaluronic acid (HA), the major components of glycocalyx, and the ability of TA to bind to elastin and type I collagen, the major components of extracellular matrix. As a result, it was confirmed that TA bound more strongly to extracellular matrix, especially elastin (see FIGS. 12~16).

The present inventors tannylated peptide drug SP (substance P) known to be effective in expanding coronary artery blood vessel or AAV9 known to be used as a delivery vehicle for a therapeutic gene, and then administered them to mice via intravenous injection. As a result, it was confirmed that they were targeted to the heart and accumulated in the heart as tannylated GFP was, indicating that the substance to be delivered to the heart could be tannylated and targeted to the heart (see FIGS. 17~22).

The present inventors have confirmed that tannylated GFP does not exhibit toxicity through ex vivo monophasic action potentials and in vivo cardiac function experiments (see FIGS. 23~27).

The present inventors induced tannylation of the basic fibroblast growth factor (bFGF), known to be used as a heart disease therapeutic drug, and administered the tannylated bFGF to MIR (myocardial ischemia reperfusion) animal model via intravenous injection. As a result, it was confirmed that the tannylated bFGF reduced the cardiac infarct size, compared with non-tannylated bFGF, and improved cardiac function similar to the level of the healthy heart (sham group) (see FIGS. 28 and 29).

According to the present invention, a heart disease therapeutic drug to be delivered to the heart can bind to the cardiac myocardium by inducing tannylation of the drug so as to make heart targeting and accumulation of the drug possible. Unlike the conventional invasive method used for the traditional drugs to be able to target the heart, the agent of the present invention can help a drug to target the heart with high efficiency just via non-invasive intravenous administration.

The pharmaceutical composition of the present invention can include any generally used carrier, diluent, excipient, or a combination of at least two of those. The pharmaceutically acceptable carrier can be any carrier that is able to deliver the active ingredient in the living body without limitation, which is exemplified by the compounds described in Merck Index, 13$^{th}$ ed., Merck & Co. Inc., such as saline, sterilized water, Ringer's solution, buffered saline, dextrose solution, maltodextrin solution, glycerol, ethanol and a mixture comprising one or more of those components. If necessary, a general additive such as antioxidant, buffer, and bacteriostatic agent can be additionally added. The composition of the present invention can be formulated in different forms including aqueous solutions, suspensions and emulsions for injection, pills, capsules, granules or tablets by mixing with diluents, dispersing agents, surfactants, binders and lubricants. The composition can further be prepared in suitable forms for each disease or according to ingredients by following the method represented in Remington's Pharmaceutical Science (Mack Publishing Company, Easton Pa., 18th, 1990).

The composition of the present invention can include one or more effective ingredients having the same or similar function to the active ingredient.

The composition of the present invention can be formulated by the method that can be performed by those in the art by using a pharmaceutically acceptable carrier and/or excipient in the form of unit dose or in multi-dose container. The formulation can be in the form of solution, suspension or emulsion in oil or water-soluble medium, extract, powder, granule, tablet or capsule. At this time, a dispersing agent or a stabilizer can be additionally included.

The present invention also provides a method for preventing, ameliorating or treating heart disease comprising a step of administering a tannylated heart disease therapeutic drug to a subject.

The tannylated heart disease therapeutic drug according to the present invention can have the characteristics described above. The subject herein can be mammals, particularly human.

The composition of the present invention can be administered either orally or parenterally, and the parenteral administration includes intracranial injection, intravenous injection, subcutaneous injection, intramuscular injection, intraperitoneal injection, transdermal administration and the like.

The effective dosage of the composition of the present invention can vary depending on the factors such as formulation method, administration method, age, weight, pathological condition of patient, diet, administration time, administration route, absorption rate of the active ingredient in the body, inactivation rate, other medicines applied together, excretion rate and response sensitivity, etc. Particularly, the preferable dose of the heart disease therapeutic drug of the present invention is 0.0001 ng/kg (body weight) ~200 mg/kg (body weight) per day.

In addition, the present invention provides a use of a tannylated heart disease therapeutic drug for the production of a drug for preventing, ameliorating or treating heart disease.

The tannylated heart disease therapeutic drug according to the present invention can have the characteristics described above.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Preparation of Tannylated GFP

<1-1> Expression and Purification of GFP

The gene encoding GFP was cloned in the modified pET28a_Tev vector, which was transformed into *E. coli* BL21RILP strain. The strain was cultured at 37° C. for more than 12 hours until $OD_{600}$ reached 0.4~0.8. The culture medium of the strain was purified, from which GFP having his-tag fused on N-terminal was obtained. The obtained GFP was purified using Ni-NTA resin and the said his-tag was eliminated using TEV protease. Size exclusion chromatography equilibrated with buffer (100 mM NaCl and 50 mM Tris-HCl) was performed to purify GFP additionally.

<1-2> Tannylation of GFP

To prepare tannylated GFP, a tannic acid (TA) solution (10 mM) and a GFP solution (pH=7.4, PBS (phosphate buffered saline) 238 μg/ml) were prepared. For the tannylation of GFP, TA and GFP solutions were mixed (at the volume ratio of 1:1) to make the [TA]/[GFP] stoichiometric ratios of 14, 72, 143, 214, 286, 714 and 1428. At the time of mixing, the concentration of GFP was fixed and the concentration of TA was diluted in PBS (pH 7.4) serially raising the concentration from 0.1 ([TA]/[GFP]=14), 0.5, 1, 1.5, 2, 5 and 10 ([TA]/[GFP]=1428) mM. All samples were allowed to stand at room temperature for 30 minutes.

For in vivo or ex vivo studies, tannylated GFP was centrifuged more than 5 times using Amicon filter (3 kDa, 0.5 mL, Millipore, Billerica, Mass., USA) and free TA was completely removed.

EXPERIMENTAL EXAMPLE 1

Analysis of Characteristics of Tannylated GFP

<1-1> Colloidal Stability of Tannylated GFP

To investigate the colloidal stability (that is, stability or aggregation) of GFP/TA solution according to the stoichiometric ratio of [TA]/[GFP], turbidity test was performed with the GFP/TA solutions having the stoichiometric ratios of 14, 72, 143, 214, 286, 714 and 1428 prepared in Example 1.

When GFP/TA complex forms an aggregation in micro scale, absorbance ($A_{600}$) increases due to the turbidity (light scattering) of the solution. The absorbance of each solution was measured. As a result, the critical stoichiometric ratio of [TA]/[GFP] was 143 (black dotted line in FIG. 2), under which no clear aggregation was observed and accordingly $A_{600}$ value was found to be almost zero. On the other hand, the turbidity of GFP/TA solution was increased gradually at the stoichiometric ratio higher than 143 and was 1.4±0.1 at the stoichiometric ratio of 1430.

As shown in photographs of the solutions with the [TA]/[GFP] ratios of 72, 143 and 357, no agglomeration was observed in the GFP/TA solution with the ratio of or 143, indicating that a nano-scale complex was formed (FIGS. 3(A) and (*b*)). However, the GFP/TA complex coagulation was observed at the [TA]/[GFP] ratio of 357, which was higher than the critical stoichiometric ratio of 143 (FIG. 3(C)).

<1-2> Size and Shape of Tannylated GFP

The size and shape of the tannylated nanocomplexes obtained from the solution with the [TA]/[GFP] stoichiometric ratio of 72 or 143 were analyzed by using AFM (atomic force microscopy, Nanoman, Veeco, USA) and DLS (dynamic light scattering).

The solution with the [TA]/[GFP] stoichiometric ratio under 143 (50 μl) was loaded on the surface of mica, followed by washing with deionized water three times. After air drying for 2 hours, the size of the tannylated nanocomplex was measured. A particle size analyzer (Zetasizer nano-ZS, Malvern instrument, UK) was also used. The sample solution (1 mL, [TA]/[GFP]=72 or 143) was placed in disposable cuvettes, followed by equilibrium for 120 seconds. Then, the size distribution of the tannylated nanocomplex was measured. As a result, the DLS hydrodynamic diameter of the tannylated GFP prepared at the [TA]/[GFP] stoichiometric ratio of 72 was 14.8±2.9 nm (FIG. 4(A), and the average dry height of the dried complex measured by AFM was approximately 10 nm (FIG. 4(B). In the case of the sample prepared at the [TA]/[GFP] stoichiometric ratio of 143, the DLS hydrodynamic diameter was increased to 52.7±21.7 nm (Figure (C)), and the average dry height of the dried complex was up to 35 nm (FIG. 4(D)).

The formation of tannylated GFP in micro-scale was also confirmed by using a fluorescence microscope (Eclipse 80i, Nikon, Japan). The tannylated GFP microaggregate was observed at the stoichiometric ratio higher than 214 (FIG. 5). As the ratio approached 714, the size of the complex was gradually increased up to 100 μm, which could be clearly detected by fluorescence microscopy (FIG. 5(C)). At the ratio of 286, a microcomplex in the average size of up to 5 μm was observed (FIG. 5(B)).

The present inventors selected GFP with the [TA]/[GFP] stoichiometric ratio of 143 for in vivo experiment because the size distribution of the tannylated GFP with the ratio of 143 was in the reasonable range of the conventional micellar nanocarriers for in vivo circulation.

EXPERIMENTAL EXAMPLE 2

In Vivo Blood Circulation and Distribution of Tannylated GFP

<2-1> Evaluation of Organ-Specific Targeting of Tannylated GFP

To investigate the in vivo circulation of tannylated proteins, the following animal test was performed. The animal test procedures were performed with the approval of Animal Care Committee, KAIST (KA2016-34), and the researchers conducted experiments according to the code of ethics recommended by Ministry of Health and Welfare.

First, in order to confirm the in vivo toxicity of tannylated GFP, weight changes of mice were observed. According to the toxicity standard measurement on mice proposed by National Cancer Institute, when a test mouse lost weight as much as 20% or up, it was considered that toxicity was confirmed. The in vivo toxicity of tannylated GFP was investigated. As a result, the mouse treated with tannylated GFP lost body weight about 6% for 2 days, which was considered not significant and then the following experiment was performed.

Tannylated GFP with the [TA]/[GFP] stoichiometric ratio of 143 or non-tannylated GFP was injected (240 μg/kg) intravenously into the tail vein of mice (BALBc, 8 weeks old, male, 24-26 g). The treated mice were sacrificed at regular intervals (3 hours and 6 hours), followed by measurement of GFP fluorescence intensities of the liver, heart, spleen, kidney and lung with IVIS imaging system (IVIS 200, Xenogen, USA). For IHC, the tissues (heart and vena cava) were fixed in 4% formaldehyde at room temperature for 48 hours, and the tissues were embedded with OCT (optimal cutting temperature) compound on dry ice. The frozen tissue block was cut into thin sections having the thickness of 10 μm using cryo-microtome (Leica CM3050s, GMI Inc., USA). The sliced sections were blocked with 1% BSA (bovine serum albumin), and then treated with anti-GFP antibody (ab6556; 1:500, Abcam, Cambridge, UK, 12 hours, 4° C.) as the primary antibody and goat-anti-rabbit IgG flamma 488 (RSA1241, 1:200, BioActs, South Korea, 1 hour, 25° C.) as the secondary antibody. The observation was performed using fluorescence microscope (Eclipse 80i, Nikon, Japan).

In the fluorescence intensity analysis of each mouse organ, fluorescence emission was not detected in most organs for 3 hours from the tannylated GFP injection (FIG. 6). However, 6 hours after the injection, the GFP derived fluorescence was mainly observed in the heart, indicating that the tannylated GFP was accumulated in the heart with high efficiency: ~$1.0 \times 10^7$~$4.9 \times 10^8$ photon $s^{-1}$ (FIG. 6, circle marked by white dotted line). When the control which was non-tannylated GFP was injected, most GFP was accumulated in the liver, and the GFP derived fluorescence was not observed in the heart neither 3 hours nor 6 hours after the injection (FIG. 7).

Heart targeting capacity of tannylation was analyzed quantitatively using HTI (heart targeting index)=[heart fluorescence emission]/[liver emission]. As a result, all the samples showed very low HTI values except the case of observation 6 hours after the injection of tannylated GFP. Particularly, HTI of non-tannylated GFP observed 3 hours after the injection was 0.007, and HTI of non-tannylated GFP observed 6 hours after the injection was 0.0025. HTI of tannylated GFP observed 3 hours after the injection was 0.0014, and HTI of tannylated GFP observed 6 hours after the injection was 0.135. These results indicate that tannylated GFP was delivered to the heart with high efficiency.

<2-2> Evaluation of Heart Targeting of Tannylated GFP Over the Time

To investigate whether or not tannylated GFP was detected in the heart 6 hours after the injection, GFP or tannylated GFP was administered to mice via intravenous injection (240 μg/kg) by the same manner as described in Experimental Example <2-1>. The mice were sacrificed at regular intervals (1.5, 5, 48 and 120 hours). GFP fluorescence intensity of the heart was measured by IVIS imaging system (IVIS 200, Xenogen, USA) and HTI values were calculated.

As a result, weak fluorescence emission ($1.7 \times 10^8 \pm 5.5 \times 10^6$ photon $s^{-1}$) was detected at 1.5 hours after the injection of tannylated GFP. Fluorescence emission was increased as much as $1.9 \times 10^8 \pm 7.8 \times 10^6$ photon $s^{-1}$ at 6 hours after the injection (FIG. 8). The fluorescence intensity was maintained at the similar level ($2.2 \times 10^8 \pm 4.4 \times 10^7$ photon $s^{-1}$) until 120 hours after the injection (FIG. 8). The results above indicate the heart targeting and heart accumulation of the tannylated protein. Time dependent HTI value was $0.124 \pm 0.015$ at 6 hours after the injection of tannylated GFP, and $0.062 \pm 0.020$ at 120 hours after the injection (FIG. 9, red rod), which were significantly different from the results of the injection of un-tannylated GFP (FIG. 9, black rod). The fluorescence signal of the heart was reduced to $1.2 \times 10^8 \pm 1.7 \times 10^7$ at 144 hours (7 days) after the injection.

<2-3> Distribution of Tannylated GFP in the Heart Tissue

To analyze the spatial distribution of tannylated GFP in the heart tissue, immunohistochemical analysis was performed as described in Experimental Example <2-1>.

Interestingly, when un-tannylated GFP was administered in the heart, fluorescence signal was not observed in any part of the heart. When tannylated GFP was administered, most fluorescence signals were emitted from the left myocardium marked by dotted line and arrow (FIG. 10(B), upper image). No fluorescence emission was observed in the inner wall of the vessel (i.e vena cava) (FIGS. 10(A) and (B), bottom images). GFP signals were observed in the myocardium close to the left ventricle as shown in the cross-sectional heart image (FIG. 10(C), white star). These results indicate that the tannylated protein was actively accumulated in the myocardium.

<2-4> Blood Circulation Time of Tannylated GFP

To investigate the blood circulation time of tannylated GFP, tannylated GFP with the [TA]/[GFP] stoichiometric ratio of 143 was injected into the tail vein of mice (240 μg/kg), and blood was collected (30-50 μl) from the tail of each mouse at regular time intervals (1.5, 5, 48 and 120 hours). To prevent blood coagulation, the collected blood was mixed with 0.2 weight % heparin solution (10 μl), followed by centrifugation at 13,500 rpm for 5 minutes to separate plasma. The obtained plasma was stored at −20° C. The amount of plasma GFP was measured using a GFP standard curve from 47.5 to 380 pg/mL with a GFP ELISA kit (Cell Biolabs, USA).

The blood circulation time of tannylated GFP (FIG. 11, red) was longer than the blood circulation time of un-tannylated GFP (FIG. 11 black). The concentration of tannylated GFP in blood flow was $8.3 \pm 0.8$ ng/mL at 8 hours after the injection (blue arrow), while the concentration of un-tannylated GFP in blood flow was 0.8±4.1 ng/mL. Most of un-tannylated GFP was discharged or filtered by the liver minutes after the injection. On the contrary, tannylated GFP remained in blood for 120 hours after the injection. The result above was consistent with the result of the investigation of the time dependent tannylated GFP accumulation in the heart, shown in FIG. 8. 420 hours after the injection of tannylated GFP, the concentration of blood GFP was maintained at a detectable level of approximately 0.3 ng/mL, but un-tannylated GFP was not detected.

EXPERIMENTAL EXAMPLE 3

Analysis of Interactions Between Tannic Acid (TA) and Extracellular Matrix (ECM) Components To investigate the interactions between TA and ECM components, the ability of TA to bind heparin sulfate (HS) and hyaluronic acid (hyaluronan, HA), the major constituents of glycocalyx, and the ability of TA to bind elastin and type I collagen, the major constituents of extracellular matrix, were analyzed by using turbidimetry method, SPR (surface plasmon resonance) and ITC (isothermal titration calorimetry). These experimental methods have been widely used to prove the interaction between biomolecules and biomaterials.

<3-1> Binding Analysis of TA and Extracellular Matrix (ECM), and TA and Glycocalyx Using Turbidimetry Method For turbidity analysis, each solution of elastin, type I collagen, HS and HA was prepared by diluting them in PBS at the concentration of 0.24 mg/mL. TA (17 mg/mL) was added to each solution at the volume ratio of 1:1, followed by mixing vigorously. Turbidity was measured at 600 nm using UV/vis spectrometer (HP8453, Hewlett-Packard, USA).

In general, when two macromolecules exhibit strong intermolecular affinity, a microcomplex is formed rapidly. This generally results in the formation of a turbid solution by scattering visible light. As expected, the turbidity ($A_{600}$) of the collagen/elastin solution was dramatically increased by the addition of TA. Precisely, the turbidity of the elastin solution was 1.219±0.022 (FIG. 12, first white bar) and the turbidity of the collagen solution was 0.173±0.022 (FIG. 12, first grey bar). However, no turbidity change was observed in the HS or HA solution.

<3-2> Binding Analysis of TA and Elastin/Type Collagen Using SPR

For SPR analysis, each solution of elastin, type I collagen (10 μg/mL) and TA (2 mg/mL) was prepared by diluting them in PBS (pH 7.3). All the solutions were filtered with 0.2 μm microfilter (Millipore, USA). Each protein (elastin or type I collagen) was adhered on Biacore gold (Au) sensor chip for 600 seconds. The chip was washed for 10 minutes to eliminate such samples attached weakly thereon. SPR analysis was performed at the flow rate of 10 μl/min using PBS as a flow buffer.

The modified response value (RU) of SPR indicates that TA had an affinity to both elastin and type I collagen (FIG. 13). When TA was exposed on the surface adsorbed with collagen, ΔRU value was 793. When TA was exposed on the surface adsorbed with elastin, ΔRU value was 1319 (FIG. 13, red. These results indicate that TA interacted with elastin more strongly.

<3-3> Binding Analysis of TA and Elastin Using ITC

Elastin (210 μg/mL) and TA (2.5 mg/mL) solutions were used for ITC analysis. Elastin was placed in a sample cell. The TA solution was placed in a syringe, which was injected to the elastin in the sample cell (250 μl) (50 sequential injections, 5 μl per injection) for titration (with stirring at 350 rpm). Time interval was set at 180 seconds for subsequent injection, and raw data was processed using Microcal Origin (Microcal Software, Northampton, USA).

The result of ITC confirmed that the interaction between TA and elastin caused thermodynamic changes (FIG. 14). The overall negative value shown in the raw data indicates the exothermic interaction for the binding between TA and elastin (FIG. 14(A)). The binding of TA-elastin was different from the thermodynamic plot of other general antigen-antibody interactions. Herein, the titration generally exhibited an S shape curve. The binding between TA and elastin was not specific but exhibited two-phase conjugation. In the first step wherein the [TA]/[elastin] ratio was up to 20 (FIG. 14(B), black arrow), TA was conjugated with elastin intermolecularly. In the second step wherein the [TA]/[elastin] ratio was 30 and up, the inter-TA/elastin complexes were conjugated each other. That is, the TA-conjugated elastin was able to play a role of nucleating seeds that can accelerate the interaction with another TA-conjugated elastin, which was confirmed by the thermodynamic transition point starting from the black arrow. In this step, the binding affinity was lower than the binding affinity between TA and elastin, so the slope was not steep compared to the first step (FIG. 14(B)).

<3-4> Binding Analysis of Tannylated GFP and ECM Using Turbidimetry

Tannylated GFP was directly added to elastin/collagen, an ECM-like solution, or to HS/HA mixture, a glycocalyx-like solution, followed by turbidimetry. Tannylated GFP (stoichiometric ratio=143, 100 μl) was added thereto instead of TA, by the same manner as described in Experimental Example <3-1>, and then turbidity of ECM or glycocalyx components (final concentration of all components=0.5 mg/mL, 100 μl) at the wavelength of 600 nm (FIG. 15).

When tannylated GFP was added to the ECM solution, the turbidity change was detectable in the $A_{600}$ value range of 0~0.2 (FIG. 15, red arrow). Similar to the turbidity test results shown in FIG. 12, no turbidity change was detected in the glycocalyx-like solution. FIG. 16 is a diagram illustrating that the tannylated protein was accumulated not in the glycocalyx but in the extracellular matrix of the heart because of the high affinity of TA for elastin/collagen.

EXAMPLE 2

Preparation of Tannylated SP (Substance P) and Tannylated mCherry-SP

It has been reported that systemic administration of SP (substance P, SEQ. ID. NO: 2), a peptide drug known to expand coronary arteries, can improve the wound healing process by promoting the migration of endogenous stem cells into the damaged tissue. Therefore, SP administration is thought to have therapeutic and regenerative effects on myocardial infarction by inducing endogenous stem cell migration to the damaged myocardium, promoting tissue regeneration and angiogenesis. Based on that, the present inventors investigated whether or not the tannylated SP was able to target the heart, like the tannylated GFP.

Tannylated SP was prepared by the same manner used for the preparation of tannylated GFP in Example 1. Particularly, tannic acid (TA) solution (10 mM) and SP solution (pH=7.4, 0.6 mM in PBS (phosphate buffered saline)) were prepared, and the concentration of the TA solution was diluted to 0.05, 0.1, 0.5 and 1 mM. The diluted TA solution and SP solution were mixed vigorously at the volume ratio of 1:1 to adjust the [SP]/[TA] stoichiometric ratios to be 10 (concentration of TA solution=0.05 mM), 5, 1 and 0.5 (concentration of TA solution=1 mM), resulting in the preparation of tannylated SP.

To analyze the in vivo heart targeting properties of tannylated SP, a mCherry tagged fusion protein (mCherry-SP) was prepared, leading to the preparation of mCherry-SP solution (mCherry-SP, 0.5 mM, $\lambda_{exc}$=587 nm, $\lambda_{emi}$=610 nm), which was further mixed with TA solution to make the [TA]/[mCherry-SP] stoichiometric ratio to be 2. As a result, tannylated mCherry-SP was prepared.

EXPERIMENTAL EXAMPLE 4

Analysis of Characteristics of Tannylated SP and Tannylated mCherry-SP

<4-1> Size and Shape of Tannylated SP

The mixed solutions with the [SP]/[TA] ratios of 20, 10, 5, 1 and 0.5 prepared to produce tannylated SP in Example 2 were observed by naked eye. Then, the size of tannylated SP ([SP]/[TA] ratio=20 and 10, volume=1 mL) was analyzed using a particle size analyzer (Zetasizer nano-ZS, Malvern instrument, UK).

As a result, it was confirmed that tannylated SP formed a complex in the size of up to 1 μm at the [SP]/[TA] ratio of 20 or 10 (FIG. 18).

<4-2> Heart Accumulation Effect of Tannylated mCherry-SP

To evaluate the in vivo heart targeting properties of tannylated SP, either un-tannylated mCherry-SP (10 μg, 0.0031 mM, 200 μl) or tannylated mCherry-SP (200 μl) prepared in Example 2 was injected into the tail vein of mice (BALBc, 8 weeks old, 24-26 g). The mice were sacrificed 6 hours after the injection. The fluorescence intensity of mCherry in the liver and in the heart was measured using an IVIS imaging system (IVIS 200, Xenogen, USA).

Similar to the results of GFP, tannylated mCherry-SP was also accumulated in the heart 6 hours after the injection (FIG. 19(A)). HTI values increased dramatically from 0.062±0.008 to 0.111±0.008 (FIG. 19(B)).

EXAMPLE 3

Preparation of Tannylated AAV9 (Adeno-Associated Virus Serotype 9)

<3-1> Preparation and Purification of AAV9 Encoding GFP

AAV9, which can be used to deliver a therapeutic gene, was tannylated to confirm that the tannylated AAV9 was targeted to the heart. AAV9 is a FDA-approved viral vector currently used in clinical tests. AAV9 was selected because tannylation of AAV9 coat protein was believed to increase the accumulation thereof in the heart.

AAV (serotype 9; AAV9) encoding GFP expressed by CMV (cytomegalovirus) promoter was prepared according to the method described in Jang, J.-H. et al., Mol. Ther. 19, 667-675 (2011). Briefly, three kinds of plasmids (equal volume, 17 μg), which were adeno helper plasmid (pHelper; Stratagene, La Jolla, Calif., USA), plasmid encoding capsid 9 assembly (pAAV9) and plasmid containing CMV FGP polynucleotide surrounded by ITRs (inverted terminal repeats), were combined with calcium phosphate to produce complexes, followed by transfecting AAV293 cells (Agilent Technologies, Palo Alto, Calif., USA). 2 days after the transfection, the AAV9 vector introduced with the GFP expression sequence was harvested and purified by iodixanol (OptiPrep, Alere Technologies AS, Oslo, Norway) density gradient ultracentrifugation (360,000 g; Optima L-90K, Beckman Coulter, Brea, Calif., USA) at 18° C. for 2 hours. Genomic titer of AAV9-GFP vector ($3.6\times10^9$ vg/μl) was determined by quantitative PCR (QPCR; Mini Opticon, Bio-rad. Hercules, Calif., USA) using SYBR green master mix (Thermo Fisher Scientific, Waltham, Mass.).

<3-2> Tannylation of AAV9

To prepare tannylated AAV9, tannylated AAV was prepared by the same manner used for the preparation of tannylated GFP in Example 1. Particularly, tannic acid (TA) solution (10 mM) and AAV9 solution prepared in Example <3-1> were prepared, and the concentration of the TA solution was diluted to 0.1, 0.25, 0.5, 0.75 and 1 mM. The diluted TA solution and AAV9 solution were mixed vigorously at the volume ratio of 1:1, resulting in the preparation of tannylated AAV9.

EXPERIMENTAL EXAMPLE 5

Evaluation of Colloidal Stability of Tannylated AAV9

Absorbance ($A_{600}$) of the tannylated AAV9 prepared in Example <3-2> was measured using UV/vis spectrometry (HP8453, Hewlett Packard).

When mixed with 0.75 mM TA solution (FIG. 20, green), AAV9 aggregate formation was observed, and therefore the maximum critical concentration for AAV9 ($1.1\times10^{10}$ vg) (FIG. 20, pink) of TA was determined to be 0.5 mM.

EXPERIMENTAL EXAMPLE 6

Evaluation of Heart Targeting of Tannylated AAV9

<6-1> Evaluation of Heart Targeting of Tannylated AAV9 in Non-Disease Model

To evaluate the in vivo heart targeting properties of tannylated AAV9, either un-tannylated AAV9 ($1\times10^{11}$ vg, 60 μl) or tannylated AAV9 ($1\times10^{11}$ vg, 60 μl) was injected into the tail vein of mice (BALBc, 8 weeks old, 24-26 g). The mice were sacrificed 21 days after the injection. The fluorescence intensity of the heart, spleen, lung, kidney and liver was measured using an IVIS imaging system (IVIS 200, Xenogen, USA).

For IHC (immunohistochemistry), the heart was fixed in 4% formaldehyde at room temperature for 48 hours, and the tissues were embedded with OCT (optimal cutting temperature) compound on dry ice. The frozen tissue block was cut into thin sections having the thickness of 10 μm using cryo-microtome (Leica CM3050s, GMI Inc., USA). To increase the permeation efficiency of antibody, Triton (0.2%) was treated thereto. The sections were blocked with 1% BSA (bovine serum albumin), and then treated with anti-GFP antibody (ab6556; 1:500, Abcam, Cambridge, UK, 12 hours, 4° C.) as the primary antibody and goat-anti-rabbit IgG flamma 488 (RSA1241, 1:200, BioActs, South Korea, 1 hour, 25° C.) as the secondary antibody. The observation was performed using fluorescence microscope (Eclipse 80i, Nikon, Japan).

The AAV9 delivered to the heart induced GFP expression, indicating that a gene cloned in AAV9 vector was expressed successfully in heart cells via cell transcription and translation (FIG. 21). The HTI value for the tannylated AAV9 complex (~0.15) was 2.5 times higher than the HTI value for the un-tannylated AAV9 (~0.06). These results suggest that tannylation did not affect the endogenous gene transfer capability of AAV9 vector.

<6-2> Evaluation of Heart Targeting of Tannylated AAV in MIR Animal Model

Heart targeting of tannylated AAV in the MIR (myocardial ischemia reperfusion) animal model was investigated.

Particularly, rats (SD rats, 8 weeks old, male, 230-270 g) were anesthetized with a mixture of isoflurane (3 cc min$^{-1}$), Rompun, xylazine (1 mg kg$^{-1}$) and oxygen in an induction chamber. Then, the rats were intubated and a mixture of isoflurane and oxygen was allowed to flow at a rate of 1 cc min$^{-1}$. The rat heart was exposed through left thoracotomy, followed by occulusion for 10 minutes. The suture line was quickly loosened to resume blood flow through the left anterior descending artery (LAD). Right after removing the suture line, the tannylated AAV9 or un-tannylated AAV9 ($2\times10^{11}$ vg, 400 μl) obtained in Example 3 was injected. Similar to the expression test in the normal heart performed in Example <6-1>, all rats were sacrificed on day 21 of the injection and GFP expression was confirmed using an IVIS system.

As a result, as shown in FIG. 22(A), tannylated AAV9 improved gene expression in the infarcted heart tissue (white dotted line), compared to AAV9 alone or untreated. After the injection of tannylated AAV9 (FIG. 22(B), green rod), GFP expression efficiency was almost twice as high as GFP expression of the group treated with AAV9 alone (red rod) or the non-treated control (black rod).

EXPERIMENTAL EXAMPLE 7

Evaluation of Cardiocytotoxicity of Tannylated GFP

To confirm the cardiocytotoxicity of tannylated GFP, ex vivo monophasic action potentials (MAP) were measured (FIGS. 23~25) and in vivo cardiac function experiments were performed (FIGS. 26 and 27).

<7-1> Recording MAP of Rat Heart

To excise the rat heart, rats were administered with heparin (1000 IU/kg) via intraperitoneal injection (ip) and anesthetized by intraperitoneal injection of pentobarbital (50 mg/kg). Once the rat was stabilized and lost pedal reflex activity, the heart was rapidly incised and the modified Krebs-Henseleit (K-H) buffer (112 mM NaCl, 5 mM KCl, 11.5 mM glucose, 25 mM NaHCO$_3$, 1.2 mM MgSO$_4$, 1.2 mM KH$_2$PO$_4$, 2 mM pyruvic acid, and 1.25 mM CaCl$_2$) saturated with carbogen (95% O$_2$ and 5% CO$_2$) was refluxed through the aorta connected to Langendorff apparatus at 37.5° C. under the pressure of 75-85 cmH$_2$O.

MAPs of the left ventricular endocardium were recorded using a modified Franz MAP electrode prepared with silver wire (0.25 mm in diameter) coated with Teflon. MAPs were continuously recorded using an electroencephalogram (EEG) amplifier (Module 73-1770, EEGA, Germany) after the initial equilibration period (15-30 minutes). The heart was electrically stimulated using differential AC amplifier 1700 (A-M System, WA) and separated pulse stimulator 2100 (A-M System, WA). Heart rate, maximum velocity ($V_{max}$) amplitude and MAP duration at 30%, 60% or 100% of maximum repolarization (APD$_{30}$, APD$_{60}$ or APD$_{100}$) were measured and continuously monitored using Ponemah software. After all those parameters were stabilized, the vehicle control (K-H solution alone) or the K-H solution containing tannylated GFP (100 μM TA+GFP, non-filtered or filtered by centrifugation) was refluxed for 15-20 minutes.

The tannylated GFP solution did not affect amplitude and $V_{max}$ parameters (FIGS. 24(A) and (B)). In the case of heart rate, 100 μM unfiltered tannylated GFP reduced heart rate from the normal 180 beats per minute to 161±16. However, filtered tannylated GFP did not affect heart rate significantly (FIG. 24(C)). This is because free tannic acid known to have toxicity was eliminated by filtration.

The present inventors also investigated the effect of tannylated GFP on the instability of heart APDs and triangulation of action potential shape in rats. The instability was quantified by short term variability (STV), and the short term variability (STV) was determined by the average orthogonal distance to the identity line on Poincare plot. Particularly, the short term variability (STV) was calculated according to the following formula: STV=Σ|D$_{n+1}$−D$_n$|/[30√2] (D: APD$_{100}$). The triangulation of the action potential shape is defined by the repolarization time from APD$_{30}$ to APD$_{100}$ (that is, triangulation of action potential shape=APD$_{100}$−APD$_{30}$). If the prolongation of action potential period observed at APD$_{100}$ is greater than the prolongation of action potential period observed at APD$_{30}$, or if the time reduction observed at APD$_{30}$ is greater than the time reduction observed at APD$_{100}$, the overall shape of the action potential becomes triangular. As shown in FIG. 25(A), when unfiltered tannylated GFP was treated, the triangulation of the action potential shape was limited. On the other hand, when filtered tannylated GFP was treated, the triangulation of the action potential shape was back to the normal level (FIG. 25(A), red box). In the case of STV, 100 μM of tannylated GFP did not affect STV significantly, similar to the non-treated control group (FIG. 25(B)).

<7-2> Measurement of Rat Heart Function Using Pressure-Volume Conductance Catheter Technique To confirm the cardiosafety of filtered tannylated GFP, in vivo cardiac hemodynamic analysis (FIG. 26) was performed.

Rats were anesthetized with 3% isoflurane (vaporizer, Vet equip. USA, 2-3 cc/min) on a heating pad with continuous body temperature monitoring. A pressure-volume converter (2.0 Fr, Millar instruments, TX) was introduced into the left ventricle through the right carotid artery, and the signals were recorded according to the informed method (Hondeghem, L. M. et al., Circulation 103, 2004-2013 (2001)). The pressure and volume signals were recorded using ScScense ADV500 (Transonic, USA) outputting data to LabScribe data collection software (iWorx/CB Sciences, USA).

After the parameter values to be recorded were stabilized, the rats were randomly divided into three groups, to which GFP (control) or tannylated GFP (12 hour group and 24 hour group) was injected into the tail vein. 12 hours and 24 hours after the injection of tannylated GFP, data was collected and analyzed.

HR (heart rate), CO (cardiac output), SV (stroke volume) and EF (ejection fraction), LV (left ventricle) pressure, dP/dt$_{max}$ (maximum dP/dt for maximum pressure rise rate), dP/dt$_{min}$ (minimum dP/dt for maximum pressure reduction rate), ESV (end systolic volume), EDV (end diastolic volume), SW (stroke work), Ea (arterial elastance) and tau values for relaxation time constant were analyzed by the following algorithm using an analysis software.

HR: 60/average cycle period
ESP: ventricular pressure at end-systole
EDP: ventricular pressure at end-diastole
LV (left ventricle) pressure: average_maximum value of pressure channel over selected cycles
dP/dt$_{max}$ average maximum value of smoothed derivative over selected cycles $dP/dt_{min}$: average minimum value of smoothed derivative over selected cycles SV=EDV (average value at end-diastole volume over selected cycles)−ESV (average value at end-systole volume over selected cycles)

CO=SV*HR

EF=100*(SV/EDV)

SW: area within the PV Loop averaged over selected cardiac cycles
Ea: ESP/SV
Tau using Weiss's method: regression of log P.

TA becomes non-toxic when it is formulated with other molecules (i.e., metal-coordinated TA complexes). So, it was assumed that the TA used for tannylation of protein fixed in molecular level did not harm. In fact, compared with when un-tannylated GFP was injected, tannylated GFP injection did not affect the parameters above 12 or 24 hours after the injection (FIG. 27). Therefore, it was confirmed from the ex vivo and in vivo analysis above that tannylated GFP did not have cardiotoxicity.

EXAMPLE 4

Preparation of Tannylated bFGF

First, bFGF (basic fibroblast growth factor, SEQ. ID. NO: 1) was dissolved in PBS (phosphate buffered saline) at the concentration of 1 mg/mL, and tannic acid (referred as TA hereinafter) solution was prepared at the concentration of 0.14 mM or 0.7 mM. TA solution (100 μl) was added to bFGF solution (0.14 mM for 5 μg, 0.7 mM for 25 μg), leading to the preparation of tannylated bFGF with the stoichiometric molar ratio ([TA]/[bFGF]) of 143.

EXPERIMENTAL EXAMPLE 8

Confirmation of Therapeutic Effect of Tannylated bFGF bFGF plays a key role in the formation of neovasculature for the recovery of heart function. However, intravenous injection of bFGF is not therapeutically effective, and thus other formulations (for example, hydrogels) need to be injected in the myocardium. Thus, it was investigated whether or not the tannylated bFGF administered via intravenous injection demonstrated therapeutic effect in MIR (myocardial ischemia reperfusion) animal model.

Particularly, rats (SD rats, 8 weeks old, male, 230-270 g) were anesthetized with a mixture of isoflurane (3 cc min$^{-1}$), Rompun, xylazine (1 mg kg$^{-1}$) and oxygen in an induction chamber. Then, the rats were intubated and a mixture of isoflurane and oxygen was allowed to flow at a rate of 1 cc min$^{-1}$. The rat heart was exposed through left thoracotomy, followed by occulusion for 10 minutes. The suture line was quickly loosened to resume blood flow through the left anterior descending artery (LAD). Right after removing the suture line, the tannylated bFGF or un-tannylated bFGF (5 μg or 25 μg, injection volume 200 μl) obtained in Example 4 was injected (n=7, each group).

28 days after the injection, in vivo hemodynamic evaluation was performed to investigate the left ventricular function using ScScense ADV500 (Transonic, USA) outputting data to LabScribe data collection software (iWorx/CB Sciences, USA).

Upon completion of the hemodynamic evaluation, the heart was separated and immersed in warm PBS (~37° C.) to eliminate blood residues. Then, the heart was quickly frozen at −20° C., and the frozen heart was sliced lengthwise approximately 2 mm away the apex. The slice was placed on a cell culture dish, which was treated with 1% TTC (triphenyltetrazolium chloride) dissolved in PBS at 37° C. for 15 minutes. After staining, the heart slice was photographed with a scanner. Then, live tissues stained with red and necrotic tissues non-stained and thus presented as white were distinguished. The size of the infarct area was measured digitally using ImageJ software, and the results are presented as %.

As a result, as shown in FIG. 28(A), 28 days after the injection of 5 μg of tannylated bFGF, the infarct size was approximately 16% of the total heart (black bar), and the infarct size of the non-treated control group was 51% (white bar). When bFGF alone was injected, the infarct size was 31% (grey bar). When 25 μg of bFGF was administered, the infarct size was not much different from when 5 μg of bFGF was administered.

Histologic images also confirmed that the size reduction of infarct after the injection of tannylated bFGF (FIG. 28(B)). In particular, the injection of tannylated bFGF recovered all the hemodynamic functional values (left ventricular pressure, stroke volume, cardiac output, and ventricular contractility index) to the similar level of the healthy heart (sham group) (FIG. 29 and Table 2). These results indicate that tannylation of a heart targeting agent is efficient in treating heart disease.

TABLE 2

|  | Sham | MIR | MIR + bFGF 5 μg | MIR + Tannylated bFGF 5 μg |
|---|---|---|---|---|
| n | 6 | 7 | 7 | 7 |
| HR, bpm | 310.0 ± 17.7 | 329.8 ± 15.2 | 316.5 ± 12.9 | 322.7 ± 18.0 |
| ESP, mmHg | 99.7 ± 1.4 | 74.3 ± 4.7** | 85.3 ± 1.7* | 103.8 ± 4.6## |
| EDP, mmHg | 8.7 ± 1.5 | 5.7 ± 1.2 | 8.5 ± 0.9 | 9.8 ± 1.6 |
| ESV, μl | 48.6 ± 11.0 | 280.2 ± 13.5** | 254.5 ± 13.8** | 133.9 ± 19.5**,## |
| EDV, μl | 255.2 ± 39.8 | 396.2 ± 13.4** | 365.3 ± 27.5* | 295.9 ± 23.3# |
| SW, mmHg · mL · kg | 3.23 ± 0.54 | 1.39 ± 0.18** | 1.51 ± 0.14* | 3.00 ± 0.53# |
| Ea, mmHg/μL | 0.57 ± 0.18 | 0.77 ± 0.21 | 0.86 ± 0.12 | 0.77 ± 0.14 |
| Tau, ms | 11.2 ± 1.1 | 10.2 ± 0.3 | 11.7 ± 0.5 | 11.7 ± 1.1 |

(compared to sham group, *P < 0.05 ( ), **P < 0.01; compared to MIR group, #P < 0.05, ##P < 0.01)

The tannylation of the present invention can be accomplished simply by mixing a material to be tannylated and tannic acid (TA) at a proper stoichiometric ratio. Tannylation increased in vivo blood circulation time similar to pegylation. However, unlike pegylation, tannylation can confer the ability to bind to the cardiac muscle of the heart, and thus it can be used for heart targeting of a tannylated material and accumulation of the same in the heart.

In this invention, GFP, SP and bFGF, the heart disease therapeutic drugs, and virus AAV9 were tannylated and it was confirmed that they were targeted and accumulated in the cardiac myocardium. Therefore, tannylation was confirmed to be useful as a general method for heart targeting of heart disease therapeutic drugs. In particular, when tannylated bFGF was intravenously injected in the MIR animal model, the therapeutic effect of the tannylated bFGF was confirmed. The results above indicate that the tannylated heart disease therapeutic drug can overcome the disadvantage of the conventional method using invasive methods to deliver the therapeutic locally to the heart.

What is claimed is:

1. A tannylated bFGF (basic fibroblast growth factor) complex consisting of bFGF and tannic acid, wherein the tannylated bFGF complex is formed by binding tannic acid to the bFGF, and wherein the tannylated bFGF complex is capable of being targeted or delivered to a heart.

2. A method of targeting or delivering bFGF (basic fibroblast growth factor) to a heart of a subject, comprising:

administering the bFGF in a form of a tannylated complex to the subject, wherein the tannylated complex consists of the bFGF and tannic acid; and wherein the tannylated complex is formed by binding the tannic acid to the bFGF.

3. The method according to claim 2, wherein the tannic acid is represented by the following structure:

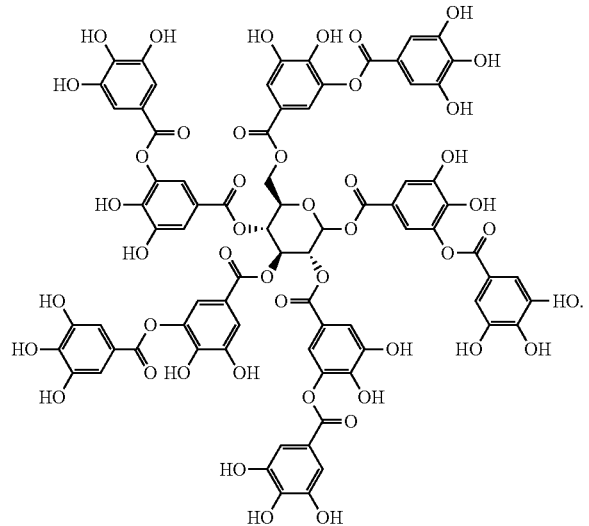

4. The method according to claim 3, wherein the tannic acid is targeted to the myocardium of the heart and accumulated therein.

5. A method of treating heart disease comprising:

administering a tannylated bFGF (basic fibroblast growth factor) complex consisting of bFGF and tannic acid, wherein the tannylated bFGF complex is formed by binding tannic acid to the bFGF; and wherein the tannylated protein complex is targeted or delivered to a heart.

6. The method according to claim 5, wherein said administering comprises via an intravenous injection.

7. The method according to claim 5, wherein said heart disease comprises ischemic heart disease.

* * * * *